(12) United States Patent
Mousa et al.

(10) Patent No.: US 9,770,419 B2
(45) Date of Patent: Sep. 26, 2017

(54) METHODS AND COMPOSITIONS OF CAMEL DERIVED PRODUCTS

(71) Applicants: Shaker A. Mousa, Wynantskill, NY (US); Abdulqader Al Haider, Riyadh (SA); Abdelgalil Abdelgader, Riyadh (SA); Abdullah M. Aldahmash, Riyadh (SA); Abdulkareem Almomen, Riyadh (SA)

(72) Inventors: Shaker A. Mousa, Wynantskill, NY (US); Abdulqader Al Haider, Riyadh (SA); Abdelgalil Abdelgader, Riyadh (SA); Abdullah M. Aldahmash, Riyadh (SA); Abdulkareem Almomen, Riyadh (SA)

( * ) Notice: Subject to any disclaimer, the term of this patent is extended or adjusted under 35 U.S.C. 154(b) by 905 days.

(21) Appl. No.: 13/953,888

(22) Filed: Jul. 30, 2013

(65) Prior Publication Data

US 2014/0037722 A1   Feb. 6, 2014

Related U.S. Application Data

(60) Provisional application No. 61/678,165, filed on Aug. 1, 2012.

(51) Int. Cl.

| | | |
|---|---|---|
| *A61K 47/42* | (2017.01) | |
| *A61K 31/726* | (2006.01) | |
| *A61K 31/728* | (2006.01) | |
| *A61K 31/738* | (2006.01) | |
| *A23C 9/152* | (2006.01) | |
| *A23P 10/30* | (2016.01) | |
| *A23L 33/19* | (2016.01) | |
| *A61K 9/48* | (2006.01) | |
| *A61K 31/337* | (2006.01) | |
| *A61K 31/704* | (2006.01) | |
| *A61K 31/12* | (2006.01) | |
| *A61K 31/727* | (2006.01) | |
| *A61K 47/48* | (2006.01) | |
| *A61K 9/51* | (2006.01) | |
| *A23G 9/00* | (2006.01) | |
| *A61K 8/63* | (2006.01) | |
| *A61K 8/64* | (2006.01) | |
| *A61Q 11/00* | (2006.01) | |
| *A61K 8/73* | (2006.01) | |
| *A61K 8/02* | (2006.01) | |
| *A61K 38/00* | (2006.01) | |

(52) U.S. Cl.
CPC ............ *A61K 9/4866* (2013.01); *A23C 9/152* (2013.01); *A23G 9/00* (2013.01); *A23L 33/19* (2016.08); *A23P 10/30* (2016.08); *A61K 8/0283* (2013.01); *A61K 8/63* (2013.01); *A61K 8/64* (2013.01); *A61K 8/73* (2013.01); *A61K 8/736* (2013.01); *A61K 9/5153* (2013.01); *A61K 9/5169* (2013.01); *A61K 31/12* (2013.01); *A61K 31/337* (2013.01); *A61K 31/704* (2013.01); *A61K 31/726* (2013.01); *A61K 31/727* (2013.01); *A61K 31/728* (2013.01); *A61K 31/738* (2013.01); *A61K 47/42* (2013.01); *A61K 47/483* (2013.01); *A61K 47/48915* (2013.01); *A61Q 11/00* (2013.01); *A23C 2260/152* (2013.01); *A23V 2002/00* (2013.01); *A61K 38/00* (2013.01); *A61K 2800/413* (2013.01)

(58) Field of Classification Search
CPC .... A61K 9/4866; A61K 47/42; A61K 31/337; A61K 31/704; A61K 31/12; A61K 31/726; A61K 31/728; A61K 47/483; A61K 47/48915; A61K 9/5153; A61K 9/5169; A61K 31/738; A61K 8/73; A61K 8/736; A23L 33/19; A23C 9/152; A23P 10/30
See application file for complete search history.

(56) References Cited

U.S. PATENT DOCUMENTS

| | | | |
|---|---|---|---|
| 7,572,448 B2 * | 8/2009 | Thorpe | ................ A61K 39/395 424/130.1 |
| 2011/0207659 A1 * | 8/2011 | Morrow | ............... A61K 31/702 514/3.1 |

OTHER PUBLICATIONS

Ehlayel et al., Camel Milk is a Safter Choice than Goat Milk for Feeding Children with Cow Milk Allergy, ISRN Allergy vol. 2011 (2011), Article ID 391641, 5 pages.*
Lesmes et al., Impact of Interfacial Composition on Physical Stability and In Vitro Lipase Digestibility of Triacylglycerol Oil Droplets Coated with Lactoferrin and/or Caseinate, J. Agric. Food Chem. 2010, 58, 7962-7969.*

(Continued)

*Primary Examiner* — Michael G Hartley
*Assistant Examiner* — Nabila Ebrahim
(74) *Attorney, Agent, or Firm* — Schmeiser, Olsen & Watts, LLP

(57) ABSTRACT

The present invention provides a composition, a dairy product, and a method for treating a disorder in a subject. The composition includes (i) polymeric nanoparticles and (ii) camel derived glycosaminoglycans (GAG)s ionic complex encapsulated into the nanoparticles, at least one active ingredient encapsulated into the nanoparticles, or combinations thereof. The nanoparticles are lactoferrin nanoparticles including camel derived lactoferrin, casein nanoparticles including camel derived casein, or combinations thereof. The dairy product includes ice cream or frozen yogurt, wherein the ice cream or frozen yogurt includes the composition and is derived from camel milk or other species of milk. The method for treating a disorder in a subject includes administering a therapeutic dose of the composition to the subject.

17 Claims, 21 Drawing Sheets

(56) References Cited

OTHER PUBLICATIONS

Gorakh Mal et al., Camel Milk and Milk Prducts, National Research Centre on Camel, P.B. No. 07, Bikaner, Rajasthan 334001 India; SMVS' Dairy Year Book 2010.*

Dehkharghanian et al. Antioxidant properties of green tea polyphenols encapsulated in caseinate beads, sciences/Springer, 2009, 89 (5).*

Conesa et al., Isolation of lactoferrin from milk of different species: Calorimetric and antimicrobial studies, Comparative Biochemistry and Physiology, Part B 150 (2008) pp. 131-139.

Khan et al., Camel Lactoferrin, a Transferrin-cum-Lactoferrin: Crystal Structure of Camel Apolactoferrin at 2.6 A Resolution and Structural Basis of its Dual Role, 2001, 209, 0022-2836/01/030751-11, pp. 751-761.

El-Fakharany et al., Effectiveness of human, camel, bovine and sheep lactoferrin on the hepatitis C virus cellular infectivity: comparison study, BioMed Central, Virology Journal, 2013 10:199, 10 pages.

Habib et al., Camel milk lactoferrin reduces the proliferation of colorectal cancer cells and exerts antioxidant and DNA damage inhibitory activities, Food Chemistry 141 (2013) pp. 148-152.

Zakaria Farah, Composition and characteristics of camel milk, Journal of Dairy Research, (1993), 60, pp. 603-626.

Baker et al., Lactoferrin and Iron: structural and dynamic aspects of binding and release, BioMetals, 17: pp. 209-216, 2004.

Legrand et al., Lactoferrin Structure and Functions, copyright Springer 2008, pp. 163-194.

Holland et al., Short Communication: Separation and quantification of caseins and casein macropeptide using ion-exchange chromatography, J. Dairy Sci. 93: pp. 893-900, doi: 10.3168/jds. 2009-2820.

\* cited by examiner

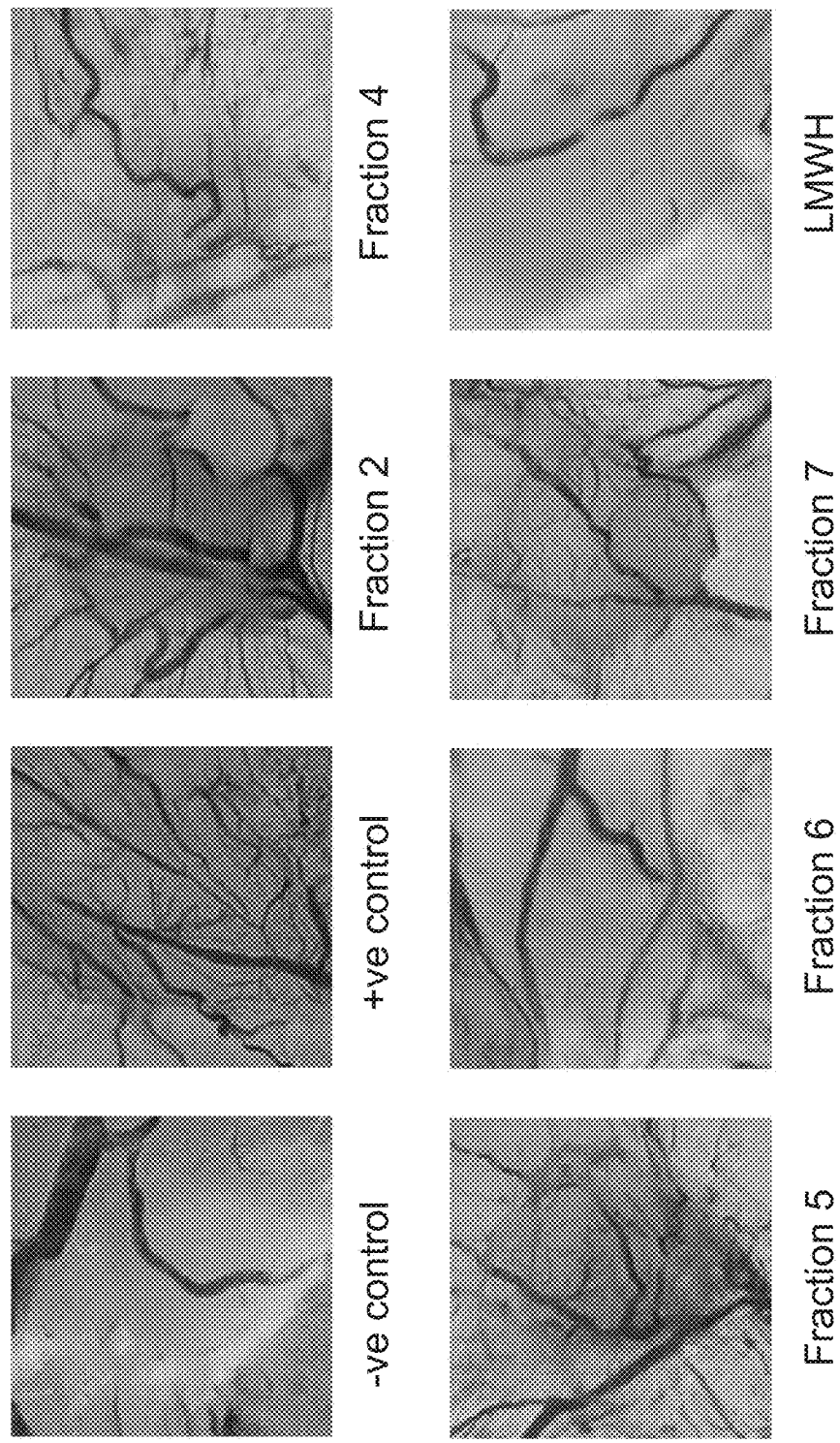

METHODS AND COMPOSITIONS OF CAMEL DERIVED PRODUCTS

CROSS-REFERENCES TO RELATED APPLICATIONS

This patent application claims priority to U.S. Provisional No. 61/678,165, filed on Aug. 1, 2012, which is incorporated herein by reference in its entirety.

TECHNICAL FIELD

This invention relates generally to a nanoparticle for use in fields such as a pharmaceutical, nutraceutical supplements or medical diagnosis, and more particularly, to camel milk derived Lactoferrin and/or casein nanoparticle comprising an active substance such as glycosaminoglycans (GAGs) substance derived from camel or other active pharmaceutical products (API), and combination thereof.

The present invention pertains to methods and compositions of camel derived biomolecules in combinations and their nanoformulations as an anti-proliferative in suppression of cancer and viral proliferation, in angiogenesis-associated disorders such as cancer, ocular neovascularization disorders, and inflammatory disorders. Additionally, Camel derived bio products can serve as a nano-carrier for targeted drug delivery in various disorders.

BACKGROUND

The use of polymer materials is expected to considerably improve storage stability and in-vivo particle stability. However, most studies use synthetic polymers produced by emulsion polymerization or the like. Although toxicity is reduced in the synthetic polymers as compared with low-molecular substances, toxicity to some extent should be expected. Therefore, a safer carrier has been demanded.

Natural polymers exhibit high structural stability as with synthetic polymers and have safety much higher than that of synthetic polymers. Thus, the natural polymers have advantages as a carrier. However, a difficult point of the natural polymer carrier as compared with synthetic polymers is a method for producing particles. Spray drying, freeze drying and jet milling can be utilized as methods for producing natural polymer particles. However, in most cases, the particle size is a micron size and is difficult to control.

Comparative survey of Lactoferrin concentration in different milks showed that biggest content of Lactoferrin is in camel milk. Camel milk has 30-100 folds higher concentrations of Lactoferrin than bovine milk. After heat treatment at 85° C. camel milk still contains 37% of Lactoferrin while bovine milk only 1.2% (Conesa C, Sánchez L, Rota C, Pérez M D, Calvo M, Farnaud S, Evans R W (2008), Isolation of lactoferrin from milk of different species: calorimetric and antimicrobial studies, Comp Biochem Physiol B Biochem Mol Biol. 150(1):131-9).

Bovine and camel Lactoferrin are homological with affinity in amount of 75%. Amino acid compound studies showed that camel Lactoferrin is rich with Met while bovine Lactoferrin is rich with Val (Conesa C, Sánchez L, Rota C, Pérez M D, Calvo M, Farnaud S, Evans R W (2008), Isolation of lactoferrin from milk of different species: calorimetric and antimicrobial studies, Comp Biochem Physio B Biochem Mol Biol. 150(1):131-9; Khan J A, Kumar P, Paramasivam M, Yadav R S, Sahani M S, Sharma S, Srinivasan A, Singh T P. (2001), Camel lactoferrin, a transferrin-cum-lactoferrin: crystal structure of camel apolactoferrin at 2.6 A resolution and structural basis of its dual role, J Mol Biol. 309(3):751-61).

Camel Lactoferrin has inhibitory effect on HCV (genotype 4a) higher than human, bovine and sheep lactoferrin (El-Fakharany E M, Sánchez L, Al-Mehdar H A, Redwan E M (2013), Effectiveness of human, camel, bovine and sheep lactoferrin on the hepatitis C virus cellular infectivity: comparison study, Virol J. 10:199. doi: 10.1186/1743-422X-10-199).

Additionally, camel milk lactoferrin was shown to inhibit the proliferation of the colon cancer cell line, HCT-116, in vitro, DNA damage and exhibits antioxidant activities (Habib H M, Ibrahim W H, Schneider-Stock R, Hassan H M. (2013), Camel milk lactoferrin reduces the proliferation of colorectal cancer cells and exerts antioxidant and DNA damage inhibitory activities, Food Chem. 141(1):148-52).

Meanwhile, camel derived Lactoferrin and/or casein are protein insoluble in water contained in camel milk (Farah Z (1993) Composition and characteristics of camel milk, J. Dairy Res. 60(4):603-26).

Since its hydrophobic portion is exposed, Lactoferrin or casein form aggregates under certain conditions. The Lactoferrin and/or casein micelles further gather and form a micelle associate of approximately 100-500 nm. Thus, LF and/or CA micelle has a wide size distribution and is aggregated when placed at acidic pH and supplemented with a sodium or potassium salt.

Glycosaminoglycans (GAGs) are classified into four groups. Heparin/heparan sulfate (HSGAGs) and chondroitin/dermatan sulfate (CSGAGs) are synthesized in the Golgi apparatus, where protein cores made in the rough endoplasmic reticulum are post-translationally modified with O-linked glycosylations by glycosyltransferases forming a proteoglycan. Keratan sulfate may modify core proteins through N-linked glycosylation or O-linked glycosylation of the proteoglycan. The fourth class of GAG, hyaluronic acid, is not synthesized by the Golgi, but rather by integral membrane synthases which immediately secrete the dynamically elongated disaccharide chain.

Lactoferrin (LF), also known as lactotransferrin, is an iron binding glycoprotein with a structure and size that closely resembles (60% sequence homology) to another iron-transporting family, the transferrins (Baker H M, Baker E N (2004), Lactoferrin and iron: structural and dynamic aspects of binding and release, Biometals 17: 209-216.)

Lower concentrations are found in plasma, bile fluids, mucosal secretions, pancreatic fluids and in neutrophils cells (Legrand D, Pierce A, Elass E, Carpentier M, Mariller C, et al. (2008). Lactoferrin structure and functions, Adv Exp Med Biol 606: 163-194.)

Structurally, LF weighs approximately 80 kDa and the polypeptide folds into two globular lobes. Each globe contains two major domains. These domains serve as the binding and glycosylation sites for iron molecules and carbonate ions. Further, depending on the amount of binding, Lf can be classified as apo-LF (iron depleted), monoferric LF (one ferric ion) and holo-Lf (two ferric ions). A possible mechanism for LF's improved binding affinity was suggested to be due to the nature of Lf to be primarily cationic with a high binding affinity to anionic ligands. Therefore this property enables LF to bind to a wide array of "Lf putative receptors" expressed in different cells and organs and aid with the internalization and absorption of LF.

A major problem with currently used cancer treatments like chemotherapy is the inability of drugs to differentiate between malignant and healthy cells leading to severe systemic toxicity. The distinguishing characteristics of NPs such as the small size, large surface-to-volume ratio allowing increased drug encapsulation and ease of functionalizing surface properties to accommodate multiple ligands that can target tumor specific markers is opening new pathways in the search for alternatives to chemotherapy. Thus utilizing natural camel LF and/or casein with or without ionic complex formation with camel derived Glycosmainoglycans (GAGs) and/or inclusion of an active substance as NPs can be a remarkable therapeutic agent, combining LF and/or casein multifunctional properties with the added benefits brought by nanotechnology.

BRIEF SUMMARY

The present invention provides a composition, comprising:
polymeric nanoparticles, wherein the nanoparticles are selected from the group consisting of lactoferrin nanoparticles comprising camel derived lactoferrin, casein nanoparticles comprising camel derived casein, and combinations thereof; and
camel derived glycosaminoglycans (GAG)s ionic complex encapsulated into the nanoparticles, at least one active ingredient encapsulated into the nanoparticles, or combinations thereof.

The present invention provides a dairy product, comprising ice cream or frozen yogurt, said ice cream or frozen yogurt comprising any of the compositions of the present invention.

The present invention provides a method for treating a disorder in a subject, said method comprising administering a therapeutic dose of any of the compositions of the present invention to the subject.

BRIEF DESCRIPTION OF THE DRAWINGS

FIG. 8C illustrates the effect of HPLC-SEC separated camel urine fractions versus LMWH on human chemo-resistant breast cancer cells (MCF7-Doxorubicin resistant) tumor angiogenesis in the CAM model, in accordance with embodiments of the present invention.

DETAILED DESCRIPTION

Figure 1:
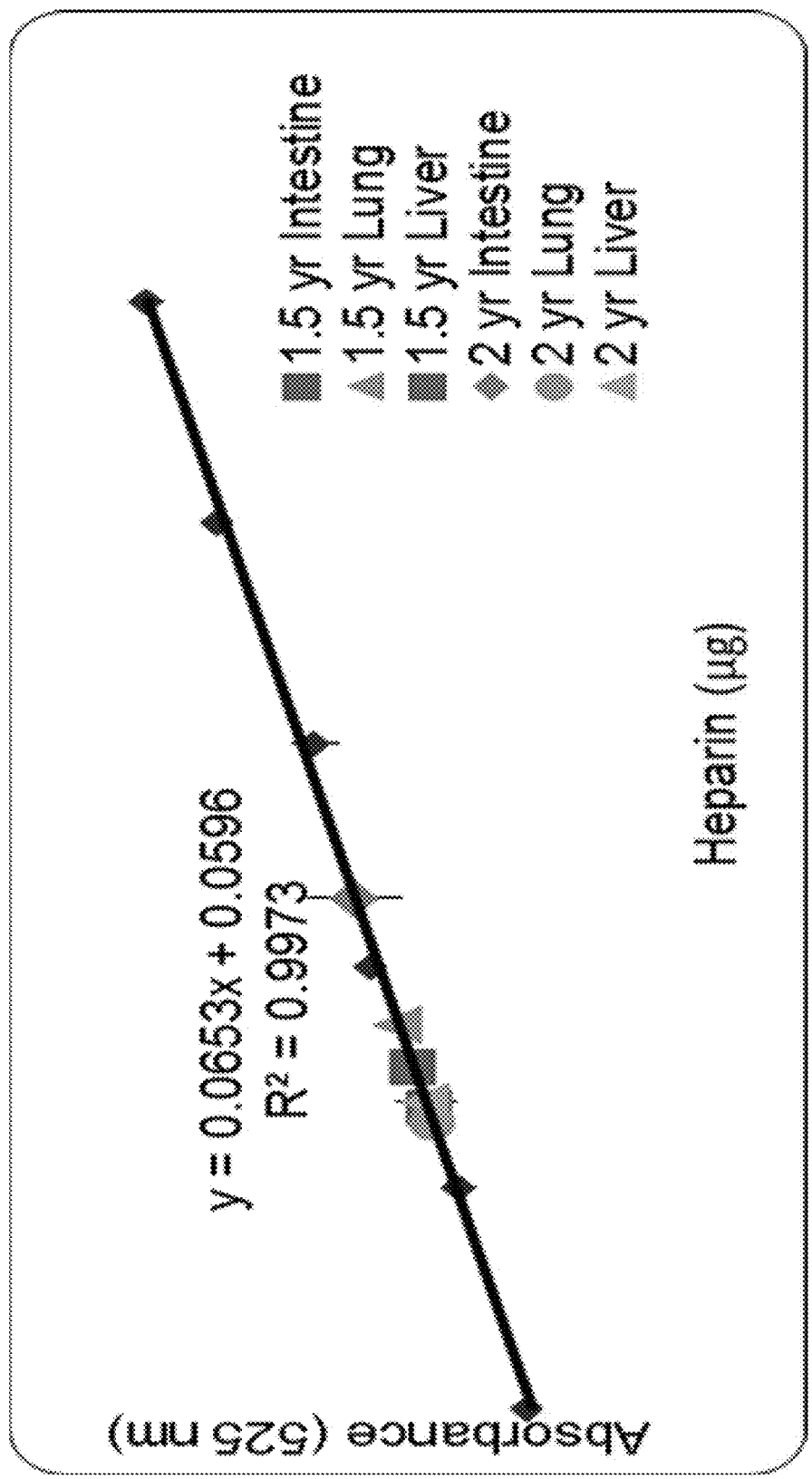
FIG. 1 depicts a carbazole assay calibration curve, in accordance with embodiments of the present invention, in accordance with embodiments of the present invention.

This invention pertains to methods and compositions of camel derived biomolecules in combinations and their nano-formulations as an anti-proliferative in suppression of, inter alia, cancer and viral proliferation, in angiogenesis-associated disorders such as cancer, ocular neovascularization disorders, and inflammatory disorders. Additionally, Camel derived bio products can serve as a nano-carrier for targeted dug delivery in various disorders.

The present invention provides a smart nanoparticle formed from camel milk derived biomolecules and forming complexes with camel urine derived biomolecules, which are produced with or without the use of surfactants and synthetic polymers, which has a controllable size ranges and is stable in the acidic range, shrink in acidic conditions and expand in basic condition and which further contains an active substance; targeting moiety.

The present invention relates to nanoformulated camel derived biomolecules such as Lactoferrin (LF) and/or casein nanoparticles or other biopolymers such as Chitosan, PLGA, metal nanoparticles or their combinations. This invention provides a composition comprising glycosaminoglycan or derivative thereof complexed ionically with camel derived Lactoferrin and/or Casein nanoparticles. Additionally, either camel derived Lactoferrin (lactotransferrin) and/or casein (alpha, beta, gamma or k forms) from camel milk can be used as a Nano carrier conjugated with other biopolymers or with each other for delivery of hydrophobic drugs.

The present invention relates to the utility of different camel derived nanoformulated compositions for use as anti-coagulant (antithrombotic), anti-cancer, anti-infectious (anti-viral, anti-bacterial, and anti-fungal), and in osteoporosis (stimulate bone formation) as Nutraceutical or pharmaceutical products.

The present invention provides a method for producing the smart nanoparticle for different therapeutic utility including, inter alia, angiogenesis-associated disorders (cancer, ocular, and inflammatory disorders), proliferative disorders (cancer, viral, and other related disorders).

The present invention provides a camel derived Lactoferrin (LF) and/or casein (CA) nanoparticle, which contains an active substance such as camel derived glycosaminoglycans (GAGs) and other known anti-cancer and anti-viral compounds, which has an average particle size between 50 nm or more and less than 500 nm, and which is produced by the following steps [(i) to (iii)]: (i) a step of mixing camel derived Lactoferrin/casein into a basic aqueous medium between pH 8.5 or more and less than pH 10.5; (ii) a step of adding camel derived GAGs and at least one type of active substance to the solution obtained in the step (i); and (iii) a step of injecting the solution obtained in the step (ii) into an acidic aqueous medium at pH (3.5 to 6.5).

Alternatively, the camel derived Lactoferrin and/or casein nanoparticle is produced by: (i) a step of mixing camel derived Lactoferrin and/or casein into a basic aqueous medium between pH 8.5 or more and less than pH 10.5; (ii) a step of adding camel derived GAGs with or without at least one type of active substance into an acidic aqueous medium at pH 3.5 to pH 6.5; and (iii) a step of injecting the solution obtained in the step (i) and step (ii) at 0.1 ml/minute rate into a common container for mixing and stirring at 30 to 60 degree Centigrade over time for the formation of nanoparticles (NPs) ranging in size from 50 nm to less than 500 nm.

Alternatively, camel casein nanoparticles containing either camel derived GAGs and/or active pharmaceutical product are coated or conjugated with camel Lactoferrin for targeted delivery.

In camel milk either Lactoferrin and/or Casein micelles form nanostructure that can be synthesized and incorporate naturally driven polyanions in camel tissues or fluids as well as natural polycations and hydrophobic drugs.

In the present invention, it was found that camel derived LF and/or CA nanoparticle with a desired size can be produced. In addition, it was also found that an active substance can be incorporated into a casein nanoparticle by utilizing the interaction between a fat-soluble active substance and a hydrophobic portion of the casein. Moreover, it was also found that such casein nanoparticles are stably present in an aqueous solution. Furthermore, it was also found that the casein nanoparticle can incorporate an ionic active substance therein by use of a mixed particle of casein with an ionic polysaccharide or with a different type of ionic protein.

Specifically, according to the present invention, a nanoparticle containing a highly safe active substance can be produced without the use of surfactants and synthetic polymers.

The camel derived LF and/or CA nanoparticle of the present invention has an average particle size usually between 50 nm or more and less than 500 nm, preferably between 50 and 250 nm.

The camel derived LF and/or CA nanoparticle of the present invention comprises at least one type of active substance. The amount of the active substance is not particularly limited. The casein nanoparticle generally comprises 0.1% to 100% by weight of the active substance with respect to the weight of casein.

In one embodiment, the casein used in the present invention may be derived from milk or from beans. Examples of such casein that can be used in the present invention include α-casein, β-casein, γ-casein, κ-casein, and the mixtures thereof. A genetically modified product can also be used. Preferably, the casein of the present invention can be used in the form of casein sodium. These caseins can be used alone or in combination of two or more types.

The method for producing the LF and/or CA nanoparticle of the present invention includes (i) a method comprising mixing casein into a basic aqueous medium solution and injecting the resulting solution into an acidic aqueous medium and (ii) a method comprising mixing casein into a basic aqueous medium solution and decreasing the pH of the resulting solution, while stirring the solution.

In one embodiment, the method comprising mixing casein into a basic aqueous medium solution and injecting the resulting solution into an acidic aqueous medium is performed by use of a syringe because of the simplicity of its operation. However, the method is not particularly limited as long as it satisfies an injection rate, solubility, a temperature, and a stirring state. In general, the solution can be injected at an injection rate of 1 mL/min to 100 mL/min. The temperature of the basic aqueous medium can be set, as appropriate. It can be normally 25° C. to 60° C., and preferably 25° C. to 70° C. The temperature of the aqueous medium can be set, as appropriate.

The type of the active substance used in the present invention can be selected from among cosmetic ingredients, functional food ingredients, and pharmaceutical ingredients, for example.

Examples of such a cosmetic ingredient include a moisturizer, a skin-lightening agent, a hair growth stimulant, a hair restorer, a hair growing agent, an anti-white hair agent, an anti-aging agent, an antioxidant, a collagen synthesis promoter, an anti-wrinkle agent, an anti-acne agent, vitamin, an ultraviolet absorber, an aromatic, a coloring agent, an anhidrotic, a cooling agent, a warming agent, a melanin generation suppressant, a melanocyte activator, a cleansing agent, and a slimming agent.

Examples of functional food ingredients for use with the present invention include vitamin, mineral, an antioxidant, an anti-stress agent, a nutritious supplement, amino acids, carotenoid, and fruit and vegetable extracts.

Examples of active pharmaceutical ingredients for use with the present invention include a hair growth stimulant, a hair restorer, a hair growing agent, an antibiotic, an anti-cancer agent, anti-viral agents for hepatitis C or other viral infection, vaccine, an anti-inflammatory agent, an anti-allergic agent, a hormone agent, an antithrombotic agent, anti-platelet agents, anticoagulants, hemostatic regulator, an immunosuppressive agent, a therapeutic agent for skin disease, an antifungal agent, an anesthetic, an antipyretic, an analgesic, an antipruritic agent, an antitussive expectorant, an antiepileptic, an anti-Parkinson agent, a sedative hypnotic, an antianxiety agent, an analeptic, an agent for psychoneurosis, a muscle relaxant, an antidepressant, a combination cold remedy, a cardiac stimulant, pro-angiogenic, anti-angiogenic agent, a vasodilator, an anti-diabetic agent, a therapeutic agent for dyslipidemia, a respiratory stimulant, an antitussive agent, vitamins, a remedy for skin disease, and a skin softener.

The aforementioned active ingredients can be used alone or in combination of two or more types.

Specific examples of moisturizer for use with the present invention are listed below. However, in the present invention, the moisturizer is not limited to these compounds and may include hyaluronic acid, flavone or isoflavone, amino acid, and collagen. The aforementioned moisturizers can be used alone or in combination of two or more types.

Specific examples of the skin-lightening agent used in the present invention are listed below. However, in the present invention, the skin-lightening agent is not limited to these compounds and may include vitamin C derivatives, hydroquinones, arbutin, and rucinol. The aforementioned skin-lightening agents can be used alone or in combination of two or more types.

Specific examples of the anti-aging agent and the antioxidant used in the present invention are listed below. However, in the present invention, the anti-aging agent and the antioxidant are not limited to these compounds and may include carotenes, retinoic acid, retinol, vitamin C derivatives, vitamin E and a derivative thereof, α-lipoic acid, coenzyme Q10, and flavonoids. The aforementioned anti-aging agents and antioxidants can be used alone or in combination of two or more types.

Specific examples of the anti-acne agent used in the present invention are listed below. However, in the present invention, the anti-acne agent is not limited to these compounds and may include salicylic acid, resorcin, retinoic acid, an aminoglycoside antibiotic, a tetracycline antibiotic, and a lincomycin antibiotic. The aforementioned anti-acne agents can be used alone or in combination of two or more types.

Specific examples of an anticancer agent used in the present invention are listed below. However, in the present invention, the anticancer agent is not limited to these compounds and may include, but are not limited to, fluorinated pyrimidine-based antimetabolites (e.g., 5-fluorouracil (5FU), tegafur, doxifluridine, and capecitabine); antibiotics (e.g., mitomycin (MMC) and Adriacin (DXR)); purine antimetabolites (e.g., folic acid antimetabolites (such as methotrexate) and mercaptopurine); active metabolites of vitamin A (e.g., antimetabolites (such as hydroxycarbamide), tretinoin, and tamibarotene); molecular target drugs (e.g., Herceptin and imatinib mesilate); platinum preparations (e.g., Briplatin or Randa (CDDP), Paraplatin (CBDC), Elplat (Oxa), and Aqupla); plant alkaloid drugs (e.g., Topotecin or Campto (CPT), taxol (PTX), Taxotere (DTX), and etoposide); alkylating agents (e.g., busulfan, cyclophosphamide, and ifomide); anti-androgen drugs (e.g., bicalutamide and flutamide); estrogen drugs (e.g., fosfestrol, chlormadinone acetate, and estramustine phosphate); LH-RH drugs (e.g., Leuplin and Zoladex); anti-estrogen drugs (e.g., tamoxifen citrate and toremifene citrate); aromatase inhibitors (e.g., fadrozole hydrochloride, anastrozole, and exemestane); corpus luteum hormone drugs (e.g., medroxyprogesterone acetate); and BCG. The aforementioned anticancer agents can be used alone or in combination of two or more types.

Specific examples of cancer to be treated include gastric, colon, pancreatic, ovarian, breast, brain, glioma, prostate, lung, renal, bladder, thyroid, lymphoma, leukemia, multiple myeloma, and other cancer types Specific examples of viral infection to be treated include hepatitis C, B, and other viral infection.

Specific examples of the anti-allergic agent used in the present invention are listed below. However, in the present invention, the anti-allergic agent is not limited to these compounds and may include: mediator release inhibitors such as sodium cromoglycate and tranilast; histamine H1 antagonists such as azelastine hydrochloride; thromboxane inhibitors such as ozagrel hydrochloride; leukotriene antagonists such as suplatast tosilate. The aforementioned anti-allergic agents can be used alone or in combination of two or more types.

Specific examples of the immunosuppressive agent used in the present invention are listed below. However, in the present invention, the immunosuppressive agent is not limited to these compounds and may include rapamycin, tacrolimus, cyclosporine, prednisolone, methylprednisolone, mycophenolate mofetil, azathioprine, and mizoribine. The aforementioned immunosuppressive agents can be used alone or in combination of two or more types.

The type of the hair growing ingredient used in the present invention is not particularly limited. Such hair growing ingredient can be selected from among cosmetic ingredients and pharmaceutical ingredients, for example. Specific examples of the hair growing ingredient contained in the protein nanoparticle of the present invention include: glycyrrhetic acid or a derivative thereof; glycyrrhizinic acid or a derivative thereof; hinokitiol; vitamin E or a derivative thereof; a vitamin C derivative; 6-benzylaminopurine; nicotinic acid amide; benzyl nicotinate; tocopherol nicotinate; nicotinic acid β-butoxy ester; isopropylmethylphenol; pentadecanoic acid or a derivative thereof; cepharanthin; finasteride; t-flavanone; an antioxidant such as carotenoid or kinetin; ethinyl estradiol; pantothenyl alcohol; pantothenyl ethyl ether; minoxidil or an analogue thereof; carpronium chloride; and adenosine. The aforementioned hair growing ingredients can be used alone or in combination of two or more types.

Specific examples of an organic solvent that is miscible at least at 10% by weight with water used in the present invention are listed below. However, in the present invention, the organic solvent is not limited to these compounds and may include water-soluble organic solvents such as ethanol, isopropanol, ethylene glycol, glycerin, acetone, and THF.

An anionic polysaccharide used in the present invention is a polysaccharide having an acidic polar group such as a carboxyl group, a sulfuric acid group, or a phosphoric acid group. Specific examples thereof are listed below. However, in the present invention, the anionic polysaccharide is not limited to these compounds and may include chondroitin sulfate, dextran sulfate, carboxymethyldextran, alginic acid, pectin, carrageenan, fucoidan, agaropectin, porphyran, karaya gum, gellan gum, xanthan gum, and hyaluronic acids.

A cationic polysaccharide used in the present invention is a polysaccharide having a basic polar group such as an amino group. Specific examples thereof are listed below. However, in the present invention, the cationic polysaccharide is not limited to these compounds and may include polysaccharides comprising glucosamine (e.g., chitin and chitosan) or galactosamine as a constituent monosaccharide.

An anionic protein used in the present invention is a protein and a lipoprotein having an isoelectric point that is located on a more basic side than the physiological pH. Specific examples thereof are listed below. However, in the present invention, the anionic protein is not limited to these compounds and may include polyglutamic acid, polyaspartic acid, cytochrome C, ribonuclease, trypsinogen, chymotrypsinogen, and α-chymotrypsin.

A cationic protein used in the present invention is a protein and a lipoprotein having an isoelectric point that is located on a more acidic side than the physiological pH. Specific examples thereof are listed below. However, in the present invention, the cationic protein is not limited to these compounds and may include polylysine, polyarginine, histone, protamine, and ovalbumin.

In one embodiment, the ionic protein and polysaccharide used in the present invention have a charge opposite to the charge of the active substance. Preferably, the amount of the ionic protein or polysaccharide added is 0.1% to 100% by weight with respect to the weight of casein.

The LF and/or CA nanoparticle of the present invention comprises the active substance therein. Such LF and/or CA nanoparticle comprising the active substance can be administered to the affected part for use. Specifically, the casein nanoparticle of the present invention is useful as a drug delivery agent.

In the present invention, the usage of the drug delivery agent is not particularly limited. For example, the drug delivery agent is used as a transdermal agent, a topical agent, an oral therapeutic agent, a cosmetic product, a supplement, and the like.

In the present invention, the drug delivery agent may comprise an additive. The type of such additive is not particularly limited. Examples of such additive include a moisturizer, a softener, a percutaneous absorption promoter, an antiseptic, a coloring agent, an aromatic, and a pH adjuster. Specific examples of the moisturizer that can be used in the present invention include, but are not limited to, agar, diglycerin, distearyldimonium hectorite, butylene glycol, polyethylene glycol, propylene glycol, sodium hyaluronate, hexylene glycol, coix seed extract, and vaserine.

Specific examples of the softener that can be used in the present invention include, but are not limited to, glycerin, mineral oil, and emollient ingredients (e.g. isopropyl isostearate, polyglyceryl isostearate, isotridecyl isononanoate, octyl isononanoate, oleic acid, glyceryl oleate, cacao butter, cholesterol, mixed fatty acid triglyceride, dioctyl succinate, sucrose acetate stearate, cyclopentanesiloxane, sucrose distearate, octyl palmitate, octyl hydroxystearate, arachidyl behenate, sucrose polybehenate, polymethylsilsesquioxane, myristyl alcohol, cetyl myristate, myristyl myristate, and hexyl laurate).

Specific examples of the percutaneous absorption promoter that can be used in the present invention include, but are not limited to, ethanol, isopropyl myristate, citric acid, squalane, oleic acid, menthol, N-methyl-2-pyrrolidone, diethyl adipate, diisopropyl adipate, diethyl sebacate, diisopropyl sebacate, isopropyl palmitate, isopropyl oleate, octyldodecyl oleate, isostearyl alcohol, 2-octyldodecanol, urea, vegetable oil, and animal oil.

Specific examples of the antiseptic that can be used in the present invention include, but are not limited to, benzoic acid, sodium benzoate, ethylparaben, potassium sorbate, sodium sorbate, sorbic acid, sodium dehydroacetate, and methylparaben.

Preferred methods of administering the LF and/or CA nanoparticle of the present invention include transdermal and transmucosal absorption. Specific examples of such administration method that can be applied in the present invention include, but are not limited to, an external liquid preparation, a poultice, an embrocation, a cleaning agent, a bath preparation, a disinfectant, an ointment, a gel, a cream, a paste, a cataplasm, a plaster, a wound surface-coating agent, a wound surface-coating gauze, a hemostatic, an adhesive, an adhesive tape, a percutaneous-absorption-type adhesive tape, a wound surface protecting agent, an aerosol, a lotion, a tonic, a liniment, an emulsion, a suspension, a saturant, a tincture, a powder, a foam, a cosmetic lotion, a massage cream, a nourishing cream, a pack, a sheet-form external skin preparation, a skin-adhesive-type cosmetic product, a lipstick, a makeup base, a foundation, a shampoo, a conditioner, a body soap, a soap, a bath form, a transnail agent, a nasal mucosal agent, an oral mucosal agent, a rectal mucosal agent, a vaginal mucosal agent, an eye mucosal agent, and a lung mucosal agent.

The dose of the LF and/or CA nanoparticle of the present invention can be set appropriately according to the body weight of a patient, the state of the disease, and so on. In general, approximately 1.0 to 100 mg per kg of body weight can be administered per administration.

The present invention will be illustrated more specifically in the following examples. However, these examples are not intended to limit the scope of the present invention.

Example 1: Isolation and Structural Characterization of Glycosaminoglycan's (GAGs) from Camel Organs GAGs were isolated and purified by using a three-step recovery and purification scheme. The procedure relied on proteolysis, ion-exchange spin column purification, and methanol precipitation. The recovered GAG samples were then analyzed with carbazole assay, polyacrylamide gel electrophoresis (PAGE) and LC-MS disaccharide analysis.

Example 2: Isolation and Purification of GAGs

Camel organ samples were lyophilized to remove excess water. Fat was removed by washing tissues with chloroform/methanol mixtures [2:1, 1:1, 1:2 (v/v)] each left overnight or for a minimum of 12 h. Liver samples were defatted; after digestion, solubilized GAGs were extracted from the tissue mixture and lyophilized, and then processed. Defatted samples were individually proteolyzed at 55° C. with solutions of Actinase E. Samples were then centrifuged and the supernatant was filtered through a 0.45 µm filter (Millipore) to remove solid particulates. After filtration, samples were lyophilized. GAGs were extracted from the isolated solids via strong anion exchange chromatography (SAX) using Vivapure Q Maxi H spin columns and collected via methanol precipitation (80% methanol (v/v) solution at 4° C. for 24 h). The resulting precipitate was isolated by centrifugation. The precipitate was reconstituted in deionized water and analyzed by carbazole assay, PAGE, and LC-MS analysis.

Example 3: Fractionation of Different Sources of Camel Urine

A standard curve consisting of various concentrations of heparin and samples of each organ isolate were mixed with sulphuric acid, which cleaves the glycosidic bonds, thereby breaking the carbohydrate chain into its composite sugar residues (FIG. 1). The uronic acids present in the mixtures then undergo a colorimetric reaction with carbazole, allowing the carbohydrate content in each sample to be quantitatively assessed.

FIG. 1 depicts a carbazole assay calibration curve, in accordance with embodiments of the present invention. The graph in FIG. 1 shows the absorbance at 525 nm for various concentrations of camel heparin and the calculated amount of GAGs in each sample.

Analysis of the different GAG contents in camel urine and milk fractions were carried out using various HPLC and preparative columns.

Figure 2:
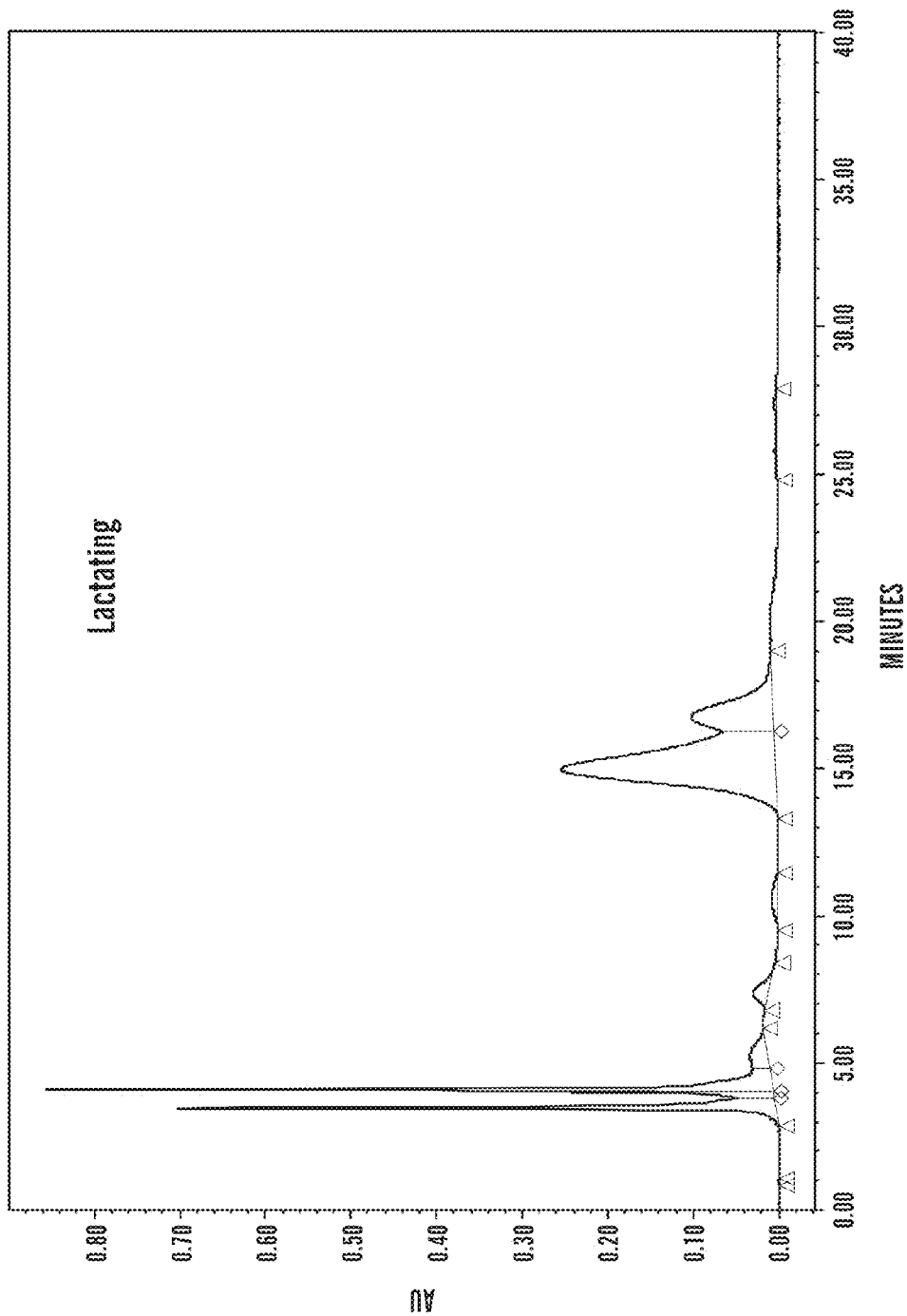
FIG. 2 depicts chromatograms of camel urine from different sources of camels which were assayed by normal-HPLC with UV scan, in accordance with embodiments of the present invention.
Figure 2:
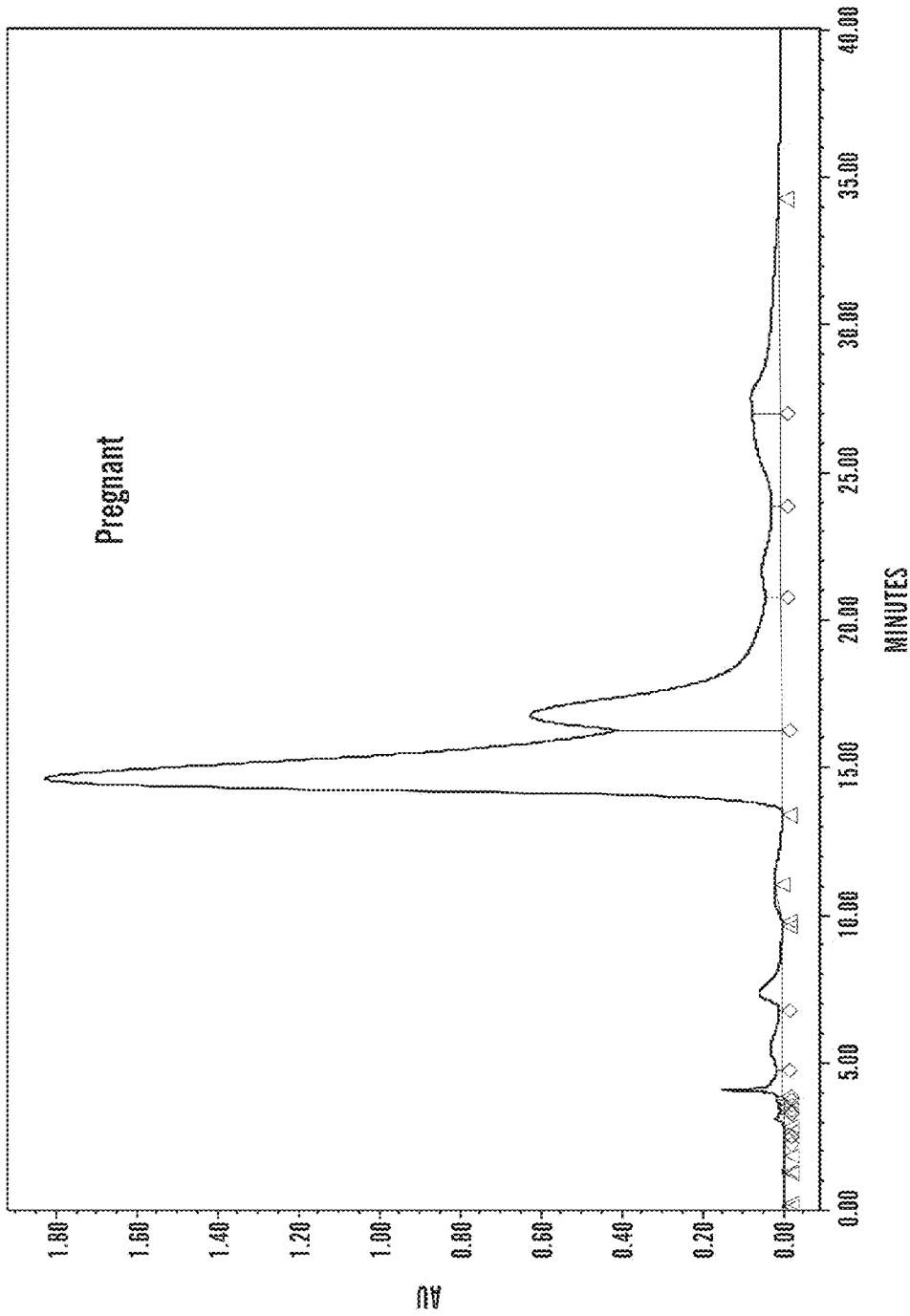
Figure 2:
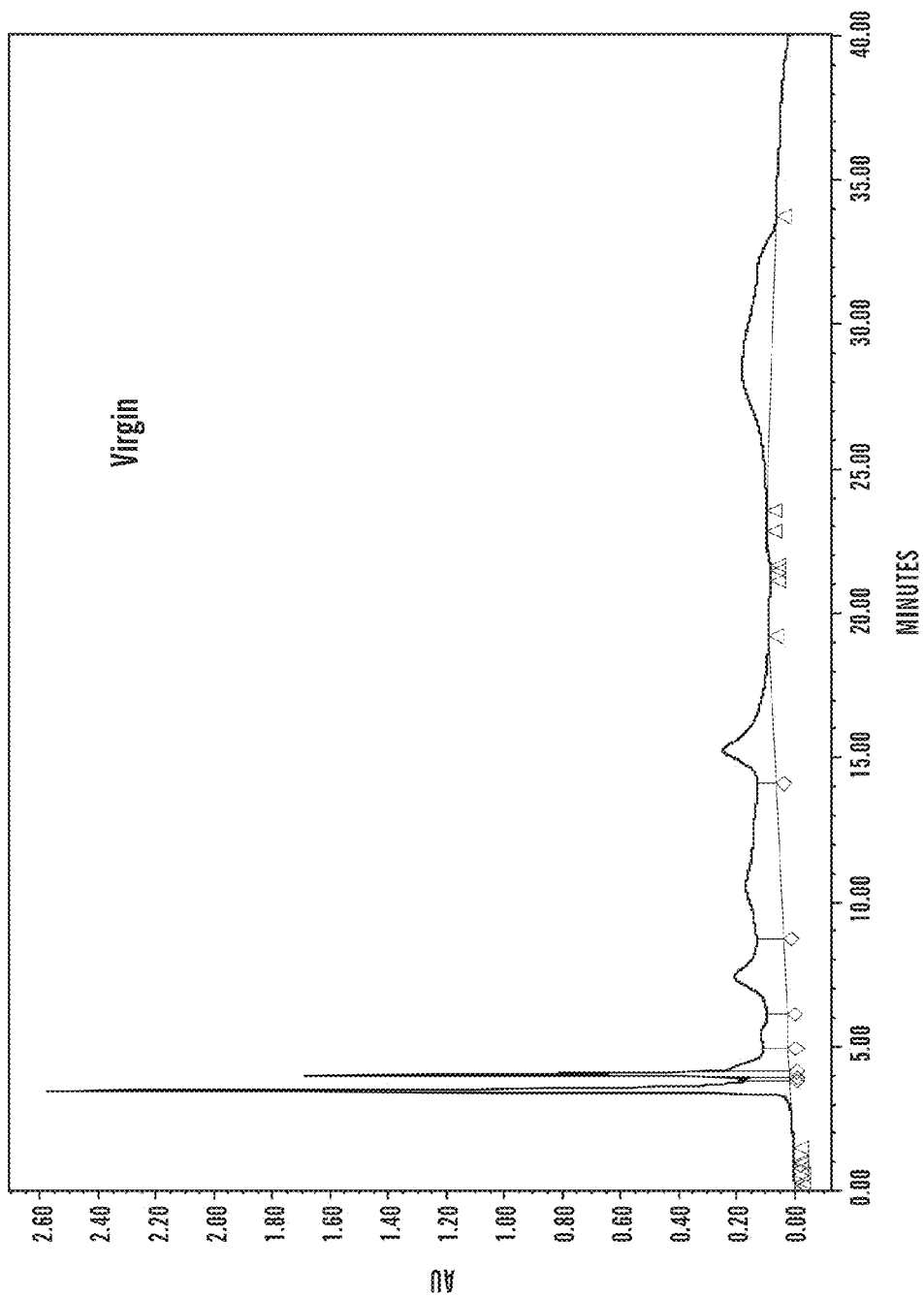

FIG. 2 depicts chromatograms of camel urine (20 µA) from different sources of camels which were assayed by normal-HPLC with UV scan (190-410 nm), in accordance with embodiments of the present invention. FIG. 2 shows a standard curve of various concentrations of heparin and samples of each organ isolate were mixed with sulphuric acid, which cleaves the glycosidic bonds, thereby breaking the carbohydrate chain into its composite sugar residues. The graph in FIG. 2 shows the absorbance at 525 nm for various concentrations of camel heparin and the calculated amount of GAGs in each sample.

Figure 3:
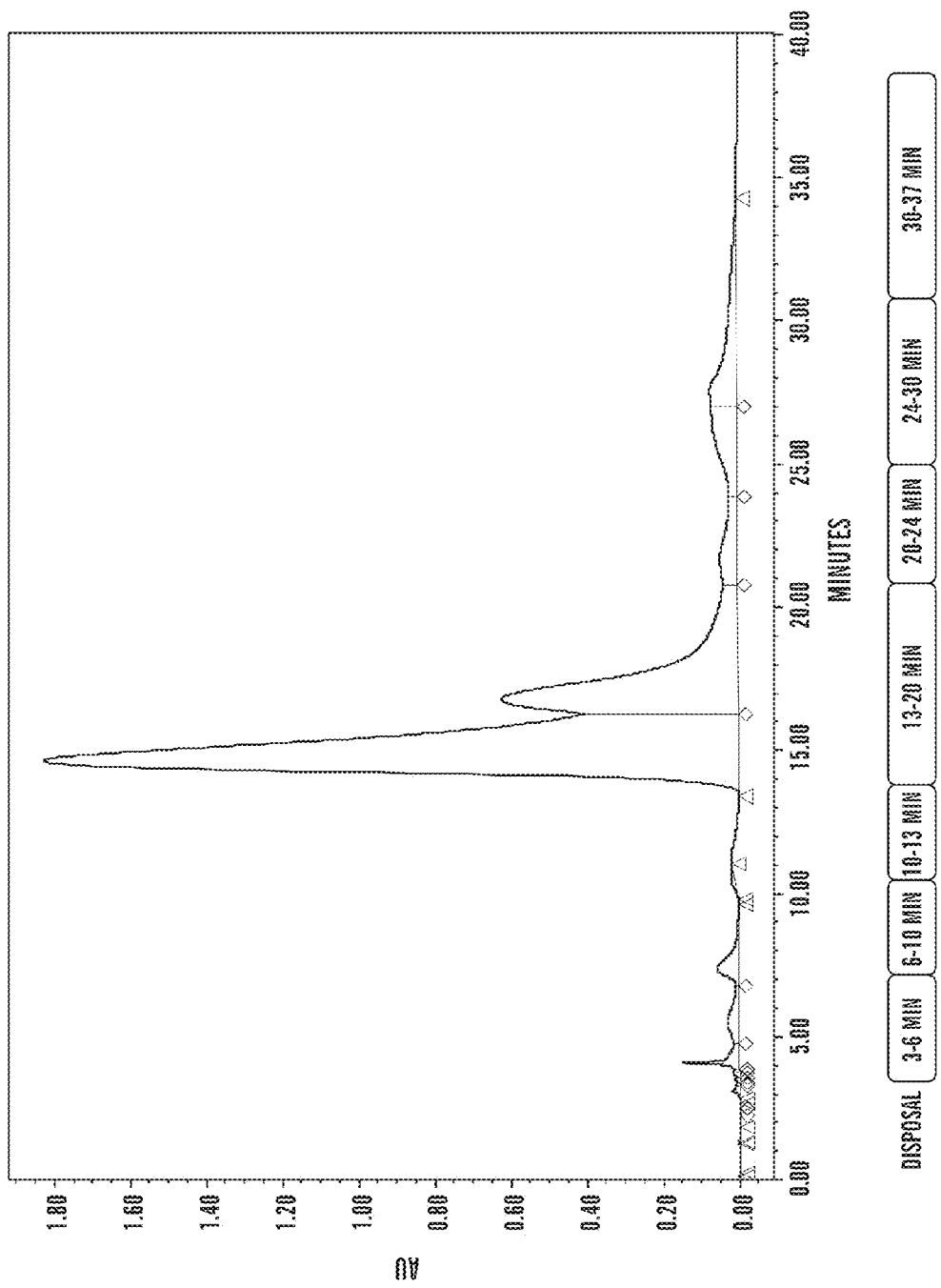
FIG. 3 illustrates the time-schedule for camel urine fraction collection of seven fractions, in accordance with embodiments of the present invention.

FIG. 3 illustrates the time-schedule for camel urine fraction collection of seven fractions (1-7), in accordance with embodiments of the present invention. An aliquot of 30 μA camel urine was injected onto a normal (NH3) HPLC column and eluted with 95% acetonitrile at 1 ml/min. The fractions were collected on the time-schedule. The fractions at same time period from three injections (90 μl of urine in total) were pooled and dried by lyophilization. These fractions 1-7 were assayed for bioactivity in the chick chorioallantoic membrane model of cancer implant to determine potential effect on tumor angiogenesis and tumor growth.

Example 4: Polyacrylamide Gel Electrophoresis (PAGE) Analysis

PAGE was applied to analyze the molecular weight and polydispersity of each sample. To each lane, ~5 ug of isolated GAGs were electrophoresed against a standard composed of heparin oligosaccharides prepared enzymatically from bovine lung heparin. The gel was visualized with Alcian blue and the molecular weights were calculated using the gel analysis software.

Example 5: Disaccharide Composition Analysis Using LCMS

Enzymatic depolymerization of GAGs: GAG samples (20 g/5 ml) were incubated with chondroitinase ABC (10 m-units) and chondroitinase ACII (5 m-units) at 37° C. for 10 h. The enzymatic products were recovered by centrifugal filtration (YM-3, 3000 MWCO, Millipore, Bedford, Mass.). The CS/DS disaccharides, which passed through the filter, were freeze-dried for LC-MS analysis. Next, heparinase I, II and III (5 m-units each) were added to the remainder, which was incubated at 37° C. for 10 h. The products were again recovered by centrifugal filtration and the heparin/HS disaccharides were similarly collected and freeze-dried for LC-MS analysis. The LC-MS analysis was performed on a LC-MS system (Agilent, LC/MSD trap MS). Solutions A and B for HPLC were 15% and 70% CAN, respectively, each also containing 37.5 mM NH4HCO3 and 11.25 mM tri-butylamine, and adjusted to pH 6.5 with acetic acid. The flow rate was 10 μl/min. The separation was performed on a C-18 column (Agilent) using solution A for 20 min, followed by a linear gradient from 20 to 45 min of 0% to 50% solution B. The column effluent entered the source of the ESI-MS for continuous detection by MS. The electrospray interface was set in negative ionization mode with the skimmer potential −40.0 V, capillary exit −120.5 V and a source of temperature of 325° C. to obtain maximum abundance of the ions in full scan spectra (150-1500 Da, 10 full scans/s). Nitrogen was used as a drying (5 liters/min) and nebulizing gas (20 p.s.i.). See Tables 1 and 2 for disaccharide composition.

TABLE 1

Chondroitin/Dermatan Sulfate Like molecules disaccharide composition analysis by LC-MS

| GAGs Sample | CS/DS disaccharides composition | | | | | | | |
|---|---|---|---|---|---|---|---|---|
| | ΔDi-0S | ΔDi-2S | ΔDi-6S | ΔDi-4S | ΔDi-diS$_B$ | ΔDi-diS$_D$ | ΔDi-diS$_E$ | ΔDi-TriS |
| 1.5 year Intestine | 4.8 | — | 22.4 | 68.8 | 0.9 | 2.5 | 0.6 | — |
| 2 year Intestine | 2.0 | — | 11.0 | 68.4 | 1.1 | 16.7 | 0.8 | — |
| 1.5 year Liver | 2.0 | — | 11.9 | 70.6 | 2.8 | 9.2 | 3.3 | 0.2 |
| 2 year Liver | 12.6 | — | 13.6 | 63.1 | 1.5 | 7.3 | 1.9 | — |
| 1.5 year Lung | 4.2 | — | 20.7 | 61.3 | 2.0 | 11.2 | 0.6 | |
| 2 year Lung | 7.6 | — | 20.1 | 59.1 | 2.1 | 11.1 | 0.1 | |

TABLE 2

Heparin Sulfate (HS)/Heparan (HP) like molecules disaccharide composition analysis by LC-MS

| GAGs Sample | HS/HP disaccharides composition | | | | | | | |
|---|---|---|---|---|---|---|---|---|
| | ΔDi-0S | ΔDi-NS | ΔDi-6S | ΔDi-2S | ΔDi-NS6S | ΔDi-NS2S | ΔDi-6S2S | ΔDi-TriS |
| 1.5 year Intestine | 13.9 | 19.3 | 19.0 | 1.1 | 9.2 | 19.8 | 1.5 | 16.3 |
| 2 year Intestine | 8.1 | 14.7 | 21.0 | 0.8 | 10.2 | 20.6 | 5.6 | 18.9 |
| 1.5 year Liver | 21.3 | 22.5 | 35.7 | 0.5 | 3.9 | 7.4 | 6.0 | 2.6 |
| 2 year Liver | 18.6 | 23.4 | 35.8 | 0.6 | 4.8 | 8.4 | 3.7 | 4.7 |
| 1.5 year Lung | 10.3 | 9.4 | 53.6 | 2.2 | 3.1 | 6.8 | 13.2 | 1.4 |
| 2 year Lung | 7.2 | 10.3 | 54.3 | 1.9 | 6.8 | 8.1 | 9.2 | 3.2 |

Example 6: Quantification of GAGs by Carbazole Assay

The data in FIG. 1 illustrates the calibration curve for standard heparin in order to calculate the concentration of the various GAGs isolated from camel oragns or urine. The isolated GAGs were subjected to carbazole assays, and the amount of GAGs in each sample was quantified using a standard, as shown in FIG. 1. The results are given in Table 3.

TABLE 3

Quantification of isolated GAGs by Carbazole assay

| Camel Organs | mg GAG (Heparin)/gram tissue |
|---|---|
| Intestine | 2.26 ± 0.02 |
| Liver | 0.1 ± 0.01 |
| Lung | 0.80 ± 0.01 |

Molecular weights, number averages, weight averages, and polydispersities of the carbohydrate samples were calculated using the Un-scan-it software, and are listed in GAGs from matching organs and displayed similar characteristics in both sets of samples, with liver tissues presenting the shortest GAG chains and lung tissue the longest (Table 4).

TABLE 4

Analysis of Isolated GAGs Properties by PAGE

| Camel Organs | Weight Average | Polydispersity |
| --- | --- | --- |
| Intestine | 15,308 | 1.45 |
| Liver | 13052 | 1.40 |
| Lung | 16,570 | 1.42 |

The utilization of biodegradable/biocompatible polymeric materials can provide unprecedented opportunities for addressing many of the current lacunas in diagnosis and therapy of breast cancer. The nanoparticulate system has a tremendous potential due to its versatility for carrying therapeutic agent along with multiple imaging probes. Also, the ability to attach a targeting moiety by modifying surface functionality make it potential tools against different types of cancer such as breast cancer or other types of cancer.

Example 7: Isolation of Camel GAGs from Urine as Per the Above Procedures

Chondroitin sulfate (CS), CS-like molecules dermatan sulfate, hyaluronic acid, keratin sulfate, and heparin/heparan sulfate fractions were isolated from camel urine.

Example 8

Isolated GAG Molecular Weight Distribution isolated from camel organs and urine versus other species using Ultra Violet (UV) detection (Table 5A and 5B):

TABLE 5A

GAG Molecular Weight Distribution Using UV Detector at 205 nm

| | Molecular Weight Components | | | | | |
| --- | --- | --- | --- | --- | --- | --- |
| GAG Source | >12 kDa | 8-12 kDa | 5-8 kDa | 2.5-5 kDa | 1.5-2.5 kDa | <1.5 kDa |
| Camel | 2 | 3 | 12 | 49 | 29 | 5 |
| Bovine | 40 | 27 | 24 | 9 | 0 | 0 |
| Porcine | 64 | 23 | 11 | 2 | 0 | 0 |

TABLE 5B

GAG Molecular Weight Distribution Using UV Detector at 205 nm

| | Molecular Weight Components | |
| --- | --- | --- |
| GAG Source | >7.5 kDa | <7.5 kDa |
| Camel | 6 | 94 |
| Bovine | 71 | 29 |
| Porcine | 90 | 10 |

Example 9: Isolated GAG Molecular Weight Distribution Isolated from Camel Organs and Urine Versus Other Species Using Refractive Index (RI) Detection (Table 6A and 6B)

TABLE 6A

GAG Molecular Weight Distribution Using RI Detector

| | Molecular Weight Components | | | | | |
| --- | --- | --- | --- | --- | --- | --- |
| GAG Source | >12 kDa | 8-12 kDa | 5-8 kDa | 2.5-5 kDa | 1.5-2.5 kDa | <1.5 kDa |
| Camel | 4 | 7 | 18 | 54 | 17 | 0 |
| Bovine | 36 | 27 | 24 | 12 | 1 | 0 |
| Porcine | 64 | 24 | 10 | 2 | 0 | 0 |

TABLE 6B

GAG Molecular Weight Distribution Using RI Detector

| | Molecular Weight Components | |
| --- | --- | --- |
| GAG Source | >7.5 kDa | <7.5 kDa |
| Camel | 12 | 88 |
| Bovine | 67 | 33 |
| Porcine | 90 | 10 |

Example 10: Isolation of Camel Casein and Lactoferrin from Milk

Lactoferrin is iron containing protein with molecular mass 76-80 kDa with 689 amino acids residues and two $Fe^{3+}$ binding centers was isolated from camel milk. The separation process was carried out using a mini-preparative cation exchange column (1 or 5 mL of column volume), using urea acetate as elution buffer at pH 3.5 with sodium chloride gradient. All 4 major casein forms were separated, and the purity of each peak was assessed using sodium dodecyl sulfate-PAGE. Purified casein fractions were also added to raw milk to confirm their elution volumes. The quantification was carried out using purified caseins in buffer as well as added directly to fresh skim milk. This method does not use organic solvents compared with the conventional method (Holland B, Rahimi Yazdi S, Ion Titapiccolo G, Corredig M (2010), Short communication: separation and quantification of caseins and casein macropeptide using ion-exchange chromatography, J Dairy Sci. 93(3):893-900).

In a procedure for isolation of Camel Milk Lactoferrin, the following steps were followed: (i) eliminate fat—by centrifuged at 8,000×g for 15 minute; (ii) eliminate casein—by precipitation with 1 M NaCH3COO buffer pH 4.5; HCl 0.1 M; (iii) filtration by 0.2 μm membrane; and (iv) fractionation using HPLC-UV.

Lactoferrin possesses various biological functions, including roles in iron metabolism, cell proliferation and differentiation, and antibacterial, antiviral, and anti-parasitic activity. Many of these functions do not appear to be connected with its iron binding ability.

The overall structure of camel apolactoferrin folds into two lobes which contain four distinct domains. Both lobes adopt open conformations indicating wide distances between the iron binding residues in the native iron-free form of Lactoferrin. The dispositions of various residues of the iron binding pocket of the N-lobe of camel apolactoferrin are similar to those of the N-lobe in human apolactoferrin, while the corresponding residues in the C-lobe show a striking similarity with those in the C-lobes of duck and hen apo-ovotransferrins. Hence, camel Lactoferrin can be termed as half Lactoferrin and half transferrin.

Example 11

A camel derived Lactoferrin and/or casein nanoparticle contains an active substance and has an average particle size between 50-200 nm by mixing Lactoferrin and/or casein into basic aqueous medium between pH 8.5-10.5; adding at least one type of active substance (camel derived GAGs) with or without anti-cancer or anti-viral agents to the basic solution; and then mixing this solution into an acidic aqueous medium at pH ranging from 3.5 to 5.5.

Example 12

Camel derived LF 100 mg and/or CA (10-100 mg) used at 10/1 and up 1/1 LF/CA (w/w) ratio or either LF or CA alone at 100 mg and 10 mg of chondroitin/dermatan sulfate, heparin/heparan sulfate, Keratan sulfate or hyaluronic acid were mixed into 1 mL of 50 mM phosphate buffer at pH 9-10. These two solutions were mixed and exposed to ultrasonic waves. Thereafter, 1 mL of the resulting mixture solution was injected into 10 mL of 100 mM phosphate buffer at pH 4-6, using a micro-syringe under gentle stirring condition and an external temperature of 45° C., so as to obtain LF and/or CA nanoparticles. The average particle size of the nanoparticles was measured with zeta size analyzer ranged from 50-200 nm.

Example 13

Camel derived LF 100 mg and/or CA (10-100 mg) used at 10/1 and up 1/1 LF/CA (w/w) ratio or either LF or CA alone at 100 mg and 10 mg from different forms of tocopherol (alpha, beta or gamma), α-lipoic acid, vitamin D3, or β-carotene was dissolved in 1 mL of ethanol. These two solutions were mixed and exposed to ultrasonic waves. Thereafter, 1 mL of the resulting mixture solution was injected into 10 mL of 100 mM phosphate buffer at pH 4-6, using a micro-syringe under gentle stirring condition and an external temperature of 45° C., so as to obtain LF and/or CA nanoparticles. The average particle size of the nanoparticles was measured with zeta size analyzer ranged from 50-200 nm.

Example 14: Camel LF and/or CA Nanoparticles by Thermal Processing

Lactoferrin is a globular protein from milk that has considerable potential as a functional ingredient in food, cosmetic and pharmaceutical applications. Using a simple thermal processing method with Camel Lactoferrin and/or Casein was found to work very well because of its heat stability unlike other species LF or CA. Light scattering, and z-potential techniques were used to provide information about the conformational changes, aggregation, and electrical charge of Camel LF and CA in aqueous solutions. The protein nanoparticles produced by thermal treatment were resistant to subsequent changes in pH (from 3 to 11) and to high level of salt addition. The Lactoferrin and/or casein nanoparticles produced provide functional ingredients in commercial products as Nutraceuticals.

The following examples pertain to GAG-Lactoferrin Nanoparticles with or without encapsulation of various API.

Example 15: Lactoferrin and/or Casein—PLGA-PEG (polyethylene gycol)) Nanoparticles Co-Encapsulating Chemotherapy for Breast Cancer and Glioma (Blood Brain Barrier Delivery)

Camel LF and/or CA were thiolated and conjugated to the distal maleimide functions surrounding on the pegylated nanoparticles to form the LF and/or CA Nanoparticles.

Example 16: Poly (Lactic-Co-Glycolic Acid) (PLGA) Coated or Conjugated with Lactoferrin The surface of PLGA NPs is coated with camel Lactoferrin (LF)/transferrin (TF) by both physical adsorption and covalent bonding. Since cancer cells have a higher demand for iron they generally overexpress the TF receptors (TFR); thus camel LF/TF was used to functionalize nanomaterials, for its potential to target cancer cells. This study has allowed comparison of Camel LF/TF-NP bio-conjugates for the same core NPs with different functional groups. These NPs are characterized in physiological phosphate buffer, to ensure the formation of mono-dispersed TF-NP bio-conjugates. These NPs were characterized by Dynamic Light Scattering, Z-potential measurements, to ensure the formation of mono-dispersed, and stable bio-coated NPs. The increase in the hydrodynamic diameters without major changes in the PDI together with the drop in the z-potential upon TF conjugation for all samples indicates formation of TF conjugated or coated NPs Example 17: Preparation of Physically Adsorbed Camel LF/TF Nanoparticles Camel LF/TF concentration was optimized preparing a series of samples with constant NP concentration (2.2 mg/ml) and multiple TF concentrations varying from 0.5 mg/ml to 5.0 mg/ml. The amount of adsorbed TF was quantified with use of protein assay after dialysis against PBS buffer. The optimal protein concentration for the adsorption, guarantying full surface coverage was found to be 2.5 mg/ml for 100 nm size particles.

Example 18: Preparation of PLGA Covalently Linked with Camel LF/TF Nanoparticles A 5 mg of camel LF/TF was dissolved in MES 50 mM pH=6 at a concentration of 2 mg/ml. PLGA-COOH NPs were dispersed in the same buffer at a concentration of 2 mg/ml. Equal volumes of each were mixed by adding particle solution drop-wise to the protein solution with intermittent shaking. The clear mixture was then left to mix in a lab incubator for 10 minutes shaking at 500 rpm, after which 5 mg of EDAC dissolved in 20 µl buffer was added. The mixture was shaken for a further 2 hours before 10 mg of glycine was added to quench the reaction. The dispersion was then dialyzed against 10 mM phosphate buffer pH 7.4 (1×24 hrs.) in 300 kDa cut-off membrane followed by dialysis against PBS (3×24 hrs.).

Doxorubicin-loaded Lactoferrin nanoparticles (Nano-Doxo) were prepared by sol-oil chemistry. HCC was induced in rats by feeding drinking water containing 100 mg/l diethyl nitrosamine for 8 weeks. Doxorubicin (Doxo) and Nano-Doxo (2 mg of drug/kg body weight) were administered IV. The results showed that Nano-Doxo is preferentially localized in liver and plasma as compared to that in heart, kidney, and spleen suggesting advantage of using Nano-Doxo in treatment of the liver cancer due to its higher bioavailability. The efficacy and safety of the Nano-Doxo and Doxo was further evaluated in terms of nodules formed on the liver. The results showed that the incidence of tumor is significantly decreased in Nano-Doxo treated rats compared to Doxo-treated rats. The higher efficacy of Nano-Doxo compared to Doxo is further confirmed by the levels of tumor-specific gene markers p53, p21, and VEGFR1. The drug-induced toxicity is evaluated in terms of cardiotoxicity by catalase and troponin, liver toxicity by SGPT and SGOT, and kidney toxicity by creatinine and blood urea. In conclusion, Nano-Doxo, with its increased bioavailability and reduced toxicity effects, is a safe and efficacious IV formulation for treatment of liver cancer.

Example 19: Camel Derived Lactoferrin/Casein Nanoparticles Encapsulating Paclitaxel A stock solution of camel derived Lactoferrin (LF) and/or Casein (CA) was prepared by dissolving in w/w ratios ranging from 10/1 and up to 1/1 ratio. A 10 mg/ml or 1.0 mg/ml LF was mixed with CA in 0.1 M phosphate-buffered saline (PBS) at pH 7.0. The entrapment of paclitaxel in LF/CA nanoparticles where paclitaxel added at 10/1 molar ratio relative LF represents an optimal ratio.

Example 20: Camel Derived Lactoferrin/Casein Nanoparticles Containing Hydrophobic Anti-Cancer or Anti-Viral Agents Aqueous Lactoferrin and/or Casein solution (2% w/v) was adjusted to pH 2.2 with hydrochloric acid. Tween 80 (1% v/v) was added as a surfactant to LF and/or Casein solution under magnetic stirring. Methylene chloride solution of chemotherapy or other hydrophobic anti-cancer or anti-viral agents as the oil phase was mixed with aqueous LF/CA phase by homogenization at a speed of 5,000×g for 15 minutes to obtain an oil-in-water emulsion. The ratio of oil and aqueous phase was 1:10 v/v. Sodium tripolyphosphate (TPP) solution (0.25% w/v) was added drop wise to the oil-in-water emulsion under gentle magnetic stirring. After 2 hours of crosslinking, nanoparticles were isolated by centrifugation at 30,000×g at 10° C. for 30 minutes, and subsequently washed several times with Phosphate buffered saline. The particles were lyophilized and stored in dry conditions at 22° C.

The size of the NPs averaged 50-200 nm, with positive zeta potential of about +5 to +15 mv. A sustained release of anti-cancer or anti-viral agent loaded was delayed as a function of the TPP crosslinking.

Example 21: Camel Derived Lactoferrin (LF) and/or Casein (CA) Nanoparticles Encapsulating Paclitaxel or Doxorubicin A stock solution of camel derived Lactoferrin (LF) and/or Casein (CA) was prepared by dissolving in w/w ratios ranging from 10/1 and up to 1/1 ratio. A 10 mg/ml or 1.0 mg/ml LF mixed with CA in 0.1 M phosphate-buffered saline (PBS) at pH 7.0. The entrapment of paclitaxel in LF/CA nanoparticles where paclitaxel added at 10/1 molar ratio relative LF represents an optimal ratio.

The LF and/or CA nanoparticles encapsulating paclitaxel demonstrated differential uptake in various prostate cancer cell lines including PC3, PC3M, Rv221, and LNCaP, with greater suppression of prostate cancer cell proliferation as compared equivalent concentrations of free paclitaxel.

The LF and/or CA nanoparticles encapsulating doxorubicin demonstrated differential uptake in glioma cancer cell lines including C6 and U87, with greater suppression of glioma cancer cell proliferation as compared equivalent concentrations of free doxorubicin.

Example 22: Camel Derived Lactoferrin (LF) and/or Casein (CA) Nanoparticles Containing Hydrophobic Anti-Cancer or Anti-Viral Agents Aqueous Lactoferrin and/or Casein solution (2% w/v) was adjusted to pH 2.2 with hydrochloric acid. Tween 80 (1% v/v) was added as a surfactant to LF and/or Casein solution under magnetic stirring. Methylene chloride solution of chemotherapy or other hydrophobic anti-cancer or anti-viral agents as the oil phase was mixed with aqueous LF/CA phase by homogenization at a speed of 5,000×g for 15 minutes to obtain an oil-in-water emulsion. The ratio of oil and aqueous phase was 1:10 v/v. Sodium tripolyphosphate (TPP) solution (0.25% w/v) was added drop wise to the oil-in-water emulsion under gentle magnetic stirring. After 2 hours of crosslinking, nanoparticles were isolated by centrifugation at 30,000×g at 10° C. for 30 minutes, and subsequently washed several times with phosphate buffered saline. The particles were lyophilized and stored in dry conditions at 22° C. The size of the NPs averaged 50-200 nm, with positive zeta potential of about +5 to +15 mv. A sustained release of anti-cancer or anti-viral agent loaded was delayed as a function of the TPP crosslinking.

Example 23: Camel Derived Lactoferrin/Casein Nanoparticles Containing Hydrophobic Active Curcuminoids of Turmeric Curcuminoids molecules, (curcumin, diacethylcurcumin and bis-demethoxy curcumin), bind to camel derived Lactoferrin and/or Casein micelle and formed complexes through hydrophobic interactions at pH 7-8 forming nanoparticles ranging in size from 100-250 nm.

Example 24

A nanoparticulate system made up of a blend of MPEG-PLGA (methoxy-polyethylene glycol-poly (lactide-co-glycolide) and maleimide-PEG-PLGA was synthesized. Lactoferrin was attached at the nanoparticle surface by coupling the amino group of Lactoferrin to the carboxyl group of MA-PEG coated particles using 1-Ethyl-3-(3-dimethylaminopropyl)-carbodimide (EDCI). These nanoparticles were prepared by double emulsion/solvent evaporation methods. Lactoferrin conjugated to PEG-PLGA, maleimide-PEG-PLGA nanoparticles were capable of encapsulation of camel derived Glycosaminoglycans (GAGs), isolated from camel intestine, lung, liver or urine including the following class of GAGs (polyanions): (a) chondroitin/dermatan sulfate, (b) heparin/heparin sulfate, (c) Keratan sulfate, (d) hyaluronic acid, and their combinations with or without different chemotherapeutic agents or co-encapsulation of both. The molecular weight of PEG in maleimide-PEG-PLGA chosen was higher than that in MPEG-PLGA, so that the maleimide function would protrude from the corona to be available for conjugating the thiolated antibody/thiolated alpha v beta 3. Thus, these nanoparticles will have the capacity for the targeted delivery to the specific site due to the conjugation of a targeting moiety on the surface by maleimide group.

Briefly, for the preparation of void PEG-PLGA nanoparticles, 100 ul of water was emulsified by continuous sonication (30 s) of 1 ml dichloromethane solution of MPEG-PLGA and maleimide-MPEG-PLGA in a ratio of 9:1. The primary emulsion was emulsified by sonication (30 s) in 2 ml of 1% PVA poly (vinylalcohol) solution. This water-in-oil-in-water emulsion was diluted in to 40 ml of 0.5% PVA solution and stirred for few minutes under magnetic stirring. Immediately after, dichloromethane was evaporated at low pressure and at 400 C by using a rotatory evaporator and a heating bath. Nanoparticles were separated by centrifugation at high speed ultra-centrifugation for further use. In case of camel derived GAGs (a-d) doped and/or Chemotherapeutics agent doped nanoparticles 100 ul of aqueous solution of camel derived GAG such GAGs plus chemotherapeutic agent was used instead of water. Conjugation of antibody against avb3 for targeted delivery of Camel derived GAGs isolated from camel urine plus chemotherapeutic was carried out by first thiolating the antibody or alpha v beta 3 by using Traut's reagent. This thiolated antibody for alpha v beta3 or Herceptin receptor (anti-HER 2) readily reacts with the maleimide group present in the surface of the nanoparticles.

PLGA encapsulating camel derived GAG Nanoparticles size (FIG. 4), encapsulation efficiencies, and release kinetics were characterized.

Figure 4:
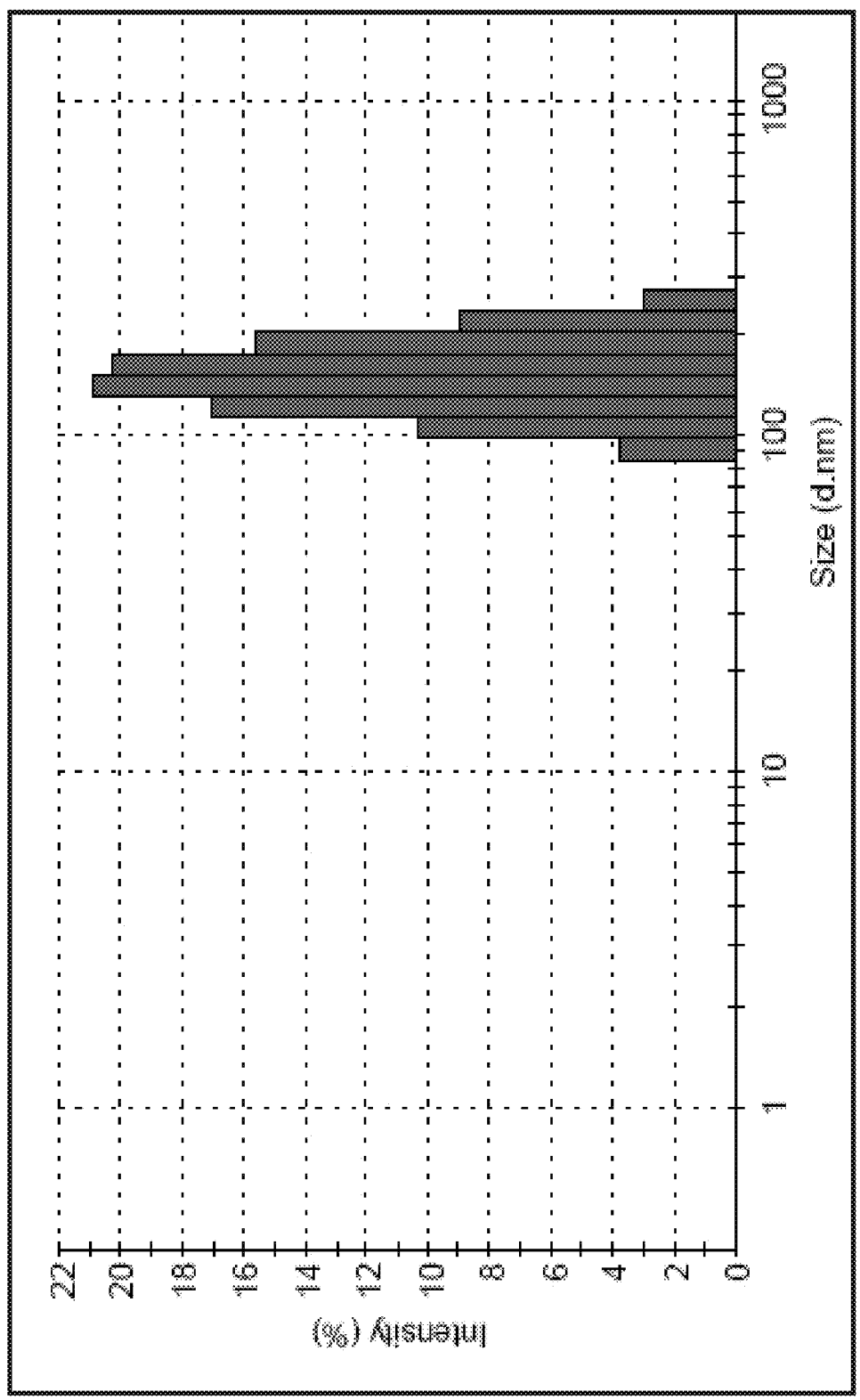
FIG. 4 depicts DLS data showing the size distribution of PLGA nanoparticles encapsulating the camel derived GAG chondroitin/dermatan sulphate, in accordance with embodiments of the present invention.

FIG. 4 depicts DLS data showing the size distribution of PLGA nanoparticles encapsulating the camel derived GAG chondroitin/dermatan sulphate, in accordance with embodiments of the present invention. The average size of the PLGA nanoparticles is about 150 nm.

Example 25: Synthesis of Targeted NP Formulations Encapsulating Camel Derived GAGs and Chemotherapy NPs comprising a blend of MPEG-PLGA (methoxypolyethylene glycol-poly lactide-co-glycolide) and maleimide-PEG-PLGA is prepared by a single emulsion method. The molecular weight of PEG in maleimide-PEG-PLGA will be chosen higher than that in MPEG-PLGA so that the maleimide functional group will protrude from the corona to be available for conjugating thiolated anti-HER2 or anti-αvβ3. For the preparation of PEG-PLGA NPs, encapsulating drugs (GAG+/−Doxorubicin or Paclitaxel, PACL) 100 ul MPEG-PLGA and maleimide-MPEG-PLGA in a ratio of 9:1 (80 mg/ml) is mixed with 20 ul of drug (20 mg/ml DMSO). This solution is added to 10 ml of 1% polyvinyl alcohol solution drop-by-drop under constant magnetic stirring, then is sonicated in for 30 seconds and stirred for another 12 hours. The solution is dialyzed to remove free drug and residual DMSO. Conjugation of the anti-HER2 or anti-αvβ3 to the surface of the drug doped NPs is achieved by first thiolating the anti-HER2 or anti-αvβ3 using Traut's reagent. The thiolated antibodies readily react with the maleimide group and the nanoformulation is lyophilized to obtain the required concentration of drug for planned studies. Methodology for NP analyses is provided below and analysis data from a typical NP formulation containing taxane compound docetaxel is shown in Figures below illustrating applications of prepared NPs.

FIG. 5 depicts the result of dynamic light scattering which shows the size of PLGA-PEG nanoparticles encapsulating docetaxel, in accordance with embodiments of the present invention. Panel (A) of FIG. 5 is a graph showing a size distribution of the PLGA-PEG nanoparticles peaking at about 200 nm. Panel (B) of FIG. 5 depicts the selected reaction monitoring (SRM) precursor to product transition for each compound. The SRM transitions of precursor ions to product ions for docetaxel were 830.3->549.1 (m/z). Panel (C) of FIG. 5 depicts a Multiple Reaction Monitoring (MRM) chromatogram of docetaxel assayed by LC-MS/MS from diluted nanoformulation and standard solution. The high sensitivity and specificity of MRM is used for selective quantification of compounds in complex mixtures. NP formulations are also characterized for surface charge using a zeta size analyzer.

Example 26: Quantification of Docetaxel by LC-MS/MS

The amount of docetaxel encapsulated (encapsulation efficiency) in the NPs was determined by LC-MS/MS. A calibration curve was generated with reference standard solutions and the amount of docetaxel encapsulated determined using this calibration curve. Methodology was developed to measure the amount of docetaxel in mouse blood plasma and in the tumor after the administration of the nanoformulation, and for heart, plasma, and tumors for Dox.

Example 27: Encapsulation Efficiency (NP Loading)

Encapsulation efficiency (NP loading) was calculated using the values for the total concentration of docetaxel in the system (free+encapsulated, $[D]_0$) and the concentration encapsulated in the nanoparticles, ($[D]f$), using the equation: E %=$([D]_f/([D]_0) \times 100$. Encapsulation efficiency for docetaxel in the NPs is 70-75%, a value typical for most chemotherapy agents previously prepared.

Figure 6:
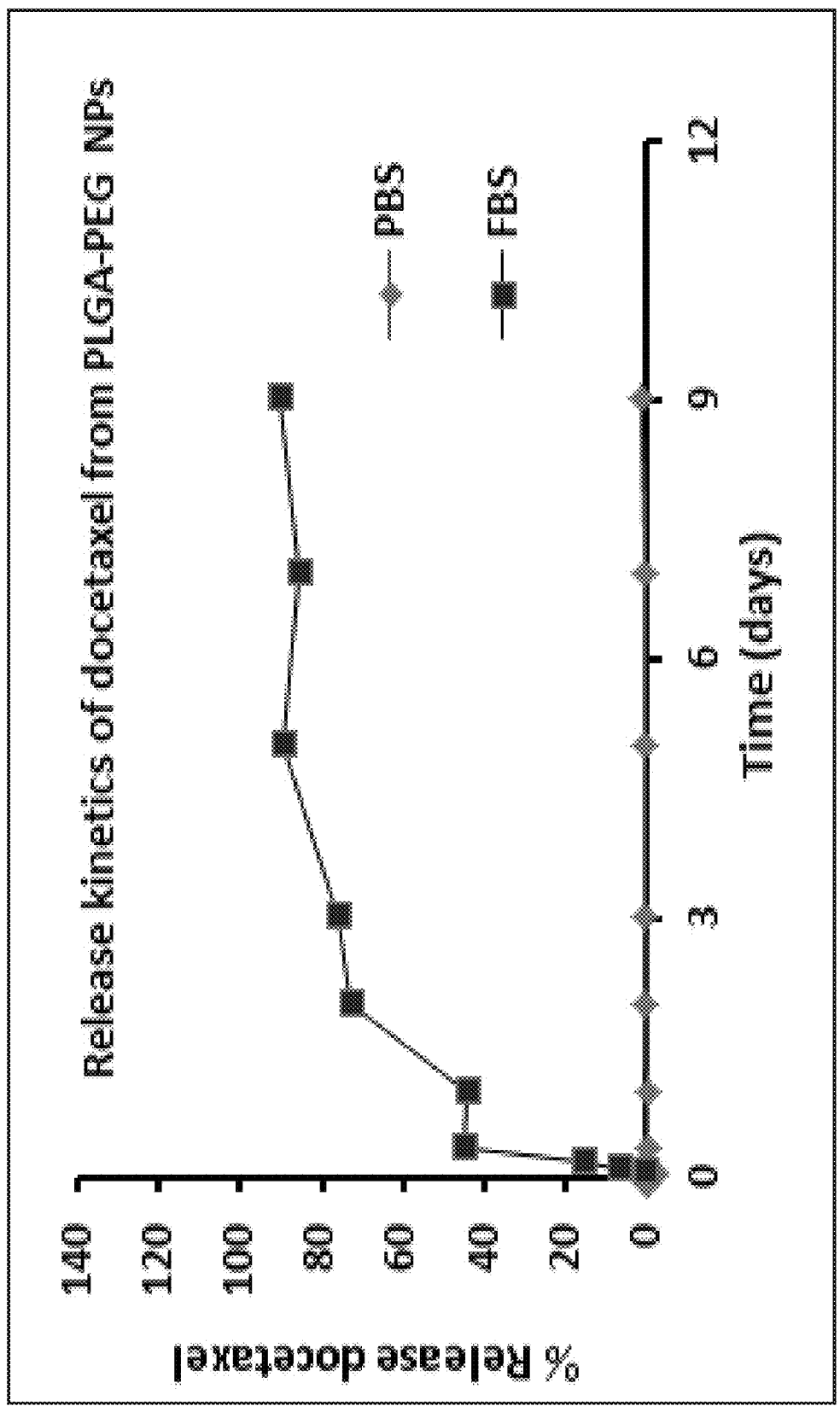
FIG. 6 depicts release kinetics of docetaxel from the nanoparticles, in accordance with embodiments of the present invention.

FIG. 6 depicts release kinetics of docetaxel from the nanoparticles, in accordance with embodiments of the present invention. A known amount of lyophilized PLGA-PEG coated with camel LF NPs encapsulating docetaxel was suspended in PBS or 20% FBS and the solution kept at room temperature. At predetermined time intervals, the solution was vortexed, and an aliquot removed and filtered through a 100 kDa cut-off membrane filter by centrifugation at 5000×g for 15 minutes to separate the released docetaxel from the PLGA-PEG-LF-NPs. The concentration of the released docetaxel was determined using LC-MS/MS. The percent release of docetaxel was calculated by using the equation: % release=$([D]f,t)/([D]0) \times 100$, where $[D]f,t$ was the concentration of docetaxel in the filtrate at time t. FIG. 6 shows the cumulative percentage of docetaxel from the NPs released at different time intervals. In FBS, there was rapid release of docetaxel (>40%) within the first 24 hours and after this time period, there was a steady but relatively slow release of docetaxel. Cumulatively, at the end of a 9 day study, it was found that around 90% of docetaxel was released in FBS whereas there was no significant release of docetaxel in PBS. Thus, this 'burst effect' within the first 24 hours releasing a significant amount of docetaxel, could be due to the presence of dissolved proteins, glucose, clotting factor polymer in serum present in FBS as well as enzymatic degradation of the PLGA polymer. Additionally, the sustained release of docetaxel in FBS shows the potential effect that these NPs might have as a nano-reservoir for docetaxel for a longer time, and thus has the potential to eliminate frequent dosing of docetaxel.

Example 28: Anti-Tumor Efficacy of NP Formulations Encapsulating Doxorubicin (Dox)+/−Heparin/Heparan Sulfate Vs. Un-Encapsulated Dox in Mice with MCF7-R (Resistance) Human Breast Tumors Mice (8/group) were inoculated with 3×106 MCF7-R cells (Dox-resistant). Treatments were begun after tumors had reached a size of 50-100 mm$^3$. All treatment groups were superior to Dox treatment alone (p<0.001), as expected in this Dox-resistant tumor. Treatment group 6, tumor vascular-targeted αvβ3-NP (αvβ3 antibody conjugated to NP surface) with encapsulated Dox+camel heparin/heparan sulfate showed inhibition that was significantly different from all treatment groups, p value vs. other groups was at least <0.02. Encapsulating Dox in αvβ3-targeted NPs or administering it with Heparin/Heparan sulfate represent potent strategies for overcoming Dox-resistance in animals bearing aggressive chemo-resistant human breast tumor.

Examples 29: Studies to Demonstrate Use of Antibody-Targeted Localization to Tumor Cells In Vivo and In Vitro NPs for treatment of pancreatic cancer were targeted to Claudin-4 (CLN4) and conjugated with camel lactoferrin which are over-expressed in both primary and metastatic pancreatic tumors using anti-CLN4 conjugated to NP surface. IVIS imaging shows results of treating mice implanted with orthotopic MPanc96-luc tumors Mice were treated with either free Dox, Void NPs—un-targeted and containing no Dox, un-targeted NP containing Dox, or CLN4-targeted NPs containing Dox. IVIS imaging demonstrates results of each treatment on tumors. In these preliminary studies, the CLN4-NP-targeting strategy appeared to be effective in localizing to pancreatic tumors, delivering anti-tumor agent Dox and limiting tumor growth and luminescent signal intensity. Void-NPs or untargeted-NPs were less effective in inhibiting tumor growth. Fluorescent signal was detected when tumors were quite small (10-50 mg), demonstrating the sensitivity of our nanoformulations in targeting to pancreatic tumors using these NP formulations. Confocal microscopy demonstrates that conjugation of CLN4 antibody to NPs facilitates binding and uptake in Panc-1 pancreatic cancer cells. Cy3 labeled NPs conjugated with CLN4 antibody and Cy3 labeled nanoparticles not conjugated to CLN4.

Example 30: Synthesize of CH-DC-NPs Encapsulating Camel Heparin/Heparan Sulfate or LMWH Derived from Camel for Oral Delivery Hybrid chitosan nanoparticles conjugated to deoxycholic acid (CH-DC-NPs) was synthesized by double emulsion solvent evaporation method. Thus, the nanoparticulate carrier system encapsulating camel derived GAGs, composed of both chitosan polymer (known to increase oral bioavailability due to its muco-adhesive properties) and deoxycholic acid (a well-known permeation enhancer) for oral bioavailability of the encapsulated GAGs.

Camel derived GAGs such as heparin/heparan sulfate, chondroitin/dermatan sulfate, Keratin sulfate or hyaluronic acid were utilized. We synthesize hybrid chitosan polymer conjugated to deoxycholic acid using crabodiimide chemistry to link free —NH2 and —COOH group present in chitosan and deoxycholic acid respectively. Later on, this hybrid polymer was used to synthesize CH-DC-NPs nanoparticles.

FIG. 5 depicts (A) size measurement of CH-DA-NPs; and (B) potential measurement of CH-DA-NPs, in accordance with embodiments of the present invention.

Example 31

The preparation of NPs was based on an oil/water emulsification-solvent evaporation method. A fixed amount of polymer (100 mg), either camel derived lactoferrin, beta casein, commercially available PLGA or their respective mixture (1:1), was used in all formulations. The matrix polymer was dissolved in 3 ml of ethyl acetate. This solution was poured into 10 ml of the aqueous phase containing the appropriate concentration of poly (vinyl alcohol) and an oil/water emulsion was formed by ultra-sonication for varying time intervals in order to obtain equivalent particle diameters of around 50-100 nm for the different NP types. The solvent was removed under reduced pressure and NPs were dialyzed (membrane pore size: 50 000 Da) against distilled water in order to remove the poly (vinyl alcohol) from the external aqueous phase. NP batches were analyzed for their size distribution and their zeta potential using a Zeta sizer (Malvern Instruments). NPs were separated from supernatant by centrifugation at 100,000×g for 30 min and the GAG derived from camel in the supernatant was quantified using carbazole assay.

Example 32: Chick Chorioallantoic Membrane (CAM) Model of Growth Factor-Induced Angiogenesis Neovascularization is examined. Ten-day old embryos purchased from Spafas, Inc. (Preston, Conn.) and incubated at 37° with 55% relative humidity were used in this investigation. A small hole is punctured in the shell concealing the air sac with a hypodermic needle and a second hole was punctured in the shell on the broadside of the egg directly over an avascular portion of the embryonic membrane, as observed during candling. A false air sac was created beneath the second hole by the application of negative pressure to the first hole, which causes the chorioallantoic membrane (CAM) to separate from the shell. A window, approximately 1.0 cm2, was cut in the shell over the dropped CAM with the use of a small crafts grinding wheel (Dermal, Division of Emerson Electric Company Racine, Wis.) allowing for direct access to the underlying CAM. Filter disks of #1 filter paper (Whatman International, United Kingdom) were soaked in 3 mg/ml cortisone acetate (Sigma, St. Louis, Mo.) in a solution of 95% ethanol and subsequently air dried under sterile conditions. Basic fibroblast growth factor (b-FGF), or other growth factors such as vascular endothelial growth factor (VEGF) were used to grow vessels on the CAMs of 10-day old chick embryos. Sterile filter disks adsorbed with b-FGF (FGF2) or VEGF dissolved in PBS are placed on growing CAMs. At 24 hours, test agent or control vehicle was added directly to CAMs topically.

Figure 7:
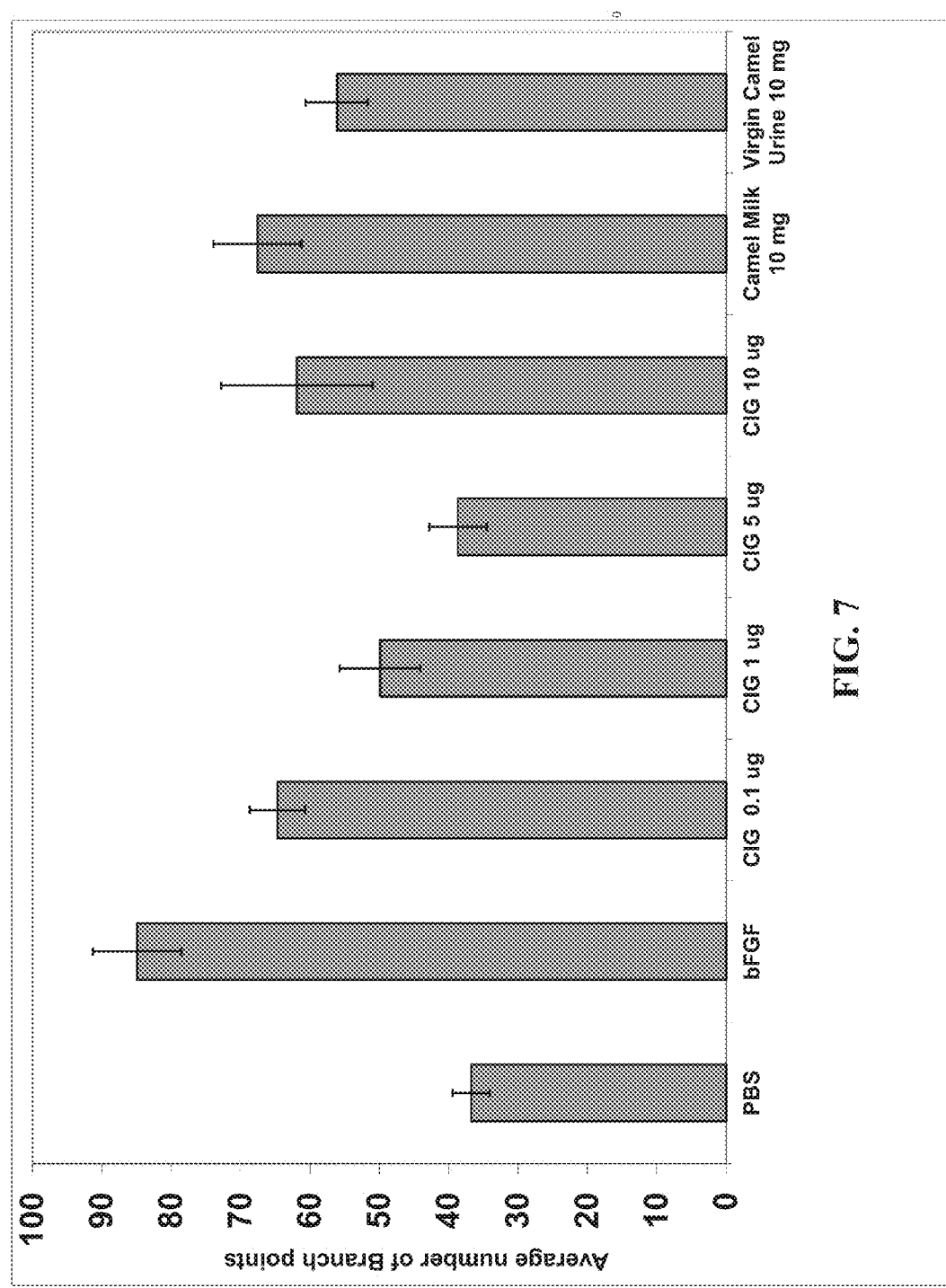
FIG. 7 depicts the effect of camel nntestine derived GAG, camel milk, and camel urine on b-FGF-induced angiogenesis in the CAM model, in accordance with embodiments of the present invention.

FIG. 7 depicts the effect of camel intestine derived GAG, camel milk, and camel urine on b-FGF-induced angiogenesis in the CAM model, in accordance with embodiments of the present invention. Camel intestine derived GAG demonstrative effective inhibition of b-FGF induced angiogenesis in the CAM model. Similarly, camel milk and camel urine demonstrated similar anti-angiogenesis activity that was further enhanced upon isolating specific fractions as shown below.

Example 33: Tumor Growth and Tumor Angiogenesis in the CAM Model

For the tumor angiogenesis and tumor growth studies, pancreatic cancer cells were implanted topically into the CAM. Test fractions, GAG or Lactoferrin were added to cancer cell implant in matrigel at into membrane of the chick egg to assess their ability to target the tumor or tumor vasculature. After 7 days of cancer cell implant, tumors were excised and examined under a stereomicroscope at 50-× magnification. Digital images of was collected using a 3-CCD color video camera system and analyzed with Image-Pro Plus software. The numbers of vessel branch points were counted for each section. Portions of the tumor were extracted for hemoglobin determinations. Individual CAMs were harvested at various time points after administration of test compounds.

Figure 5A:
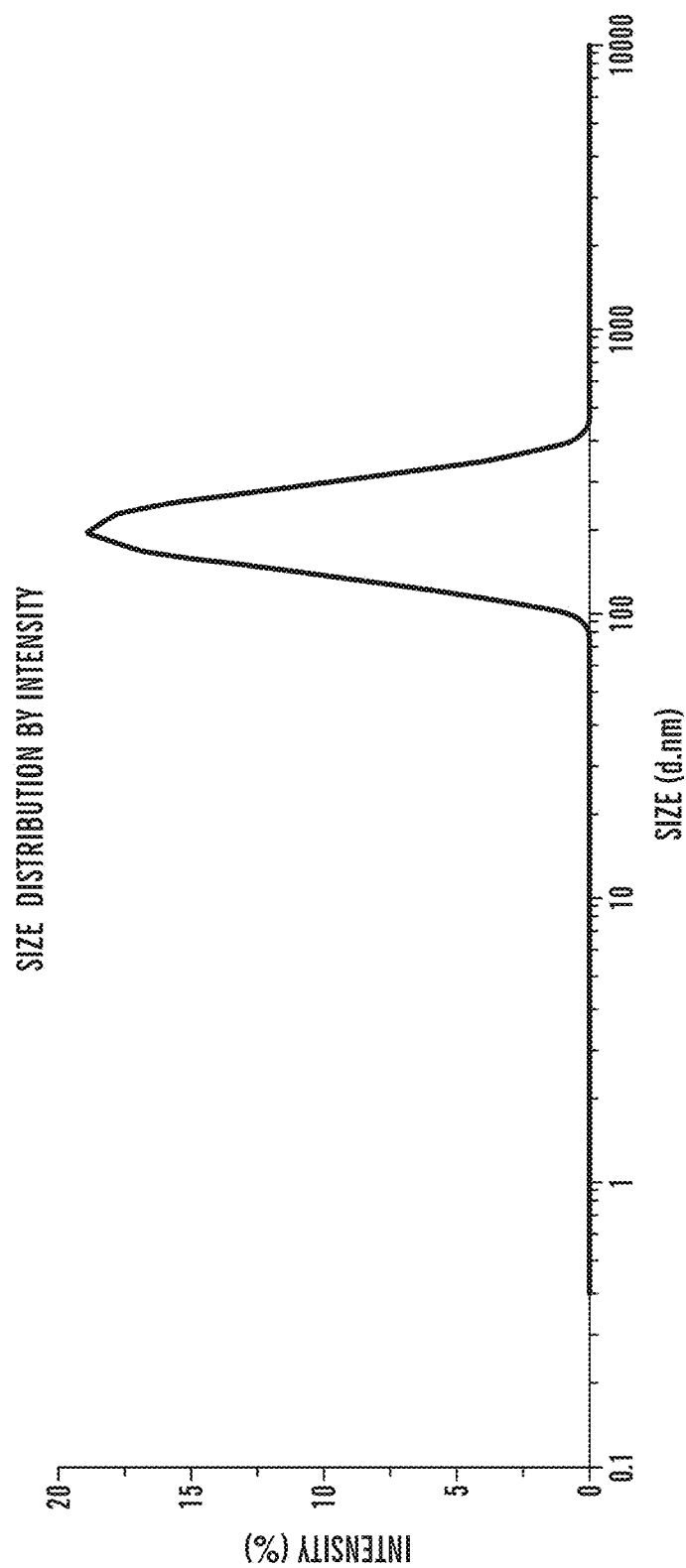
FIG. 5 depicts the result of dynamic light scattering which shows the size of PLGA-PEG nanoparticles encapsulating docetaxel, in accordance with embodiments of the present invention.
Figure 5A:
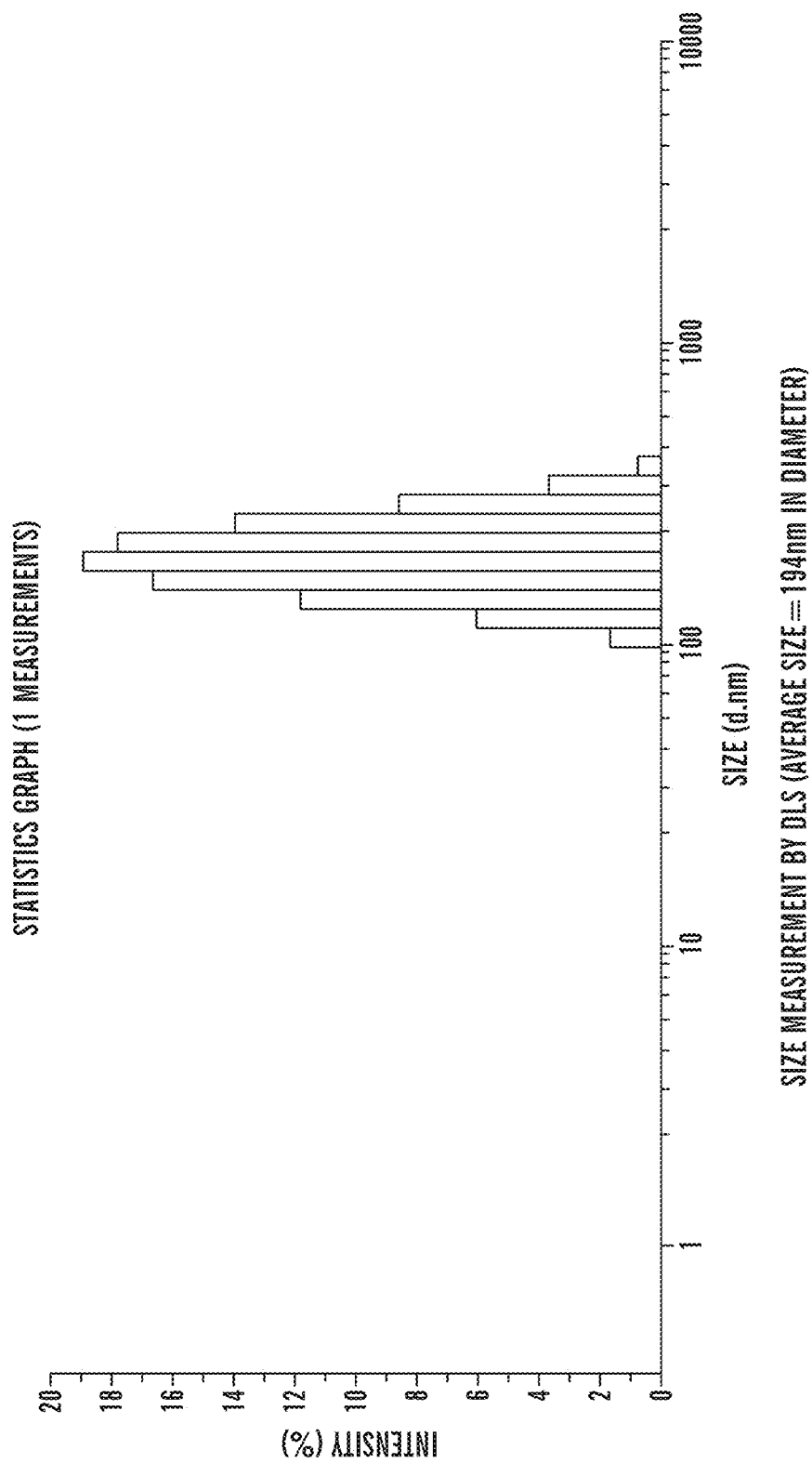

The data demonstrated significant anti-cancer efficacy for the different camel urine fractions against breast cancer (MCF7) breast cancer chemo-resistant cell line. Fractions 5-7 demonstrated greater anti-cancer efficacy where the levels of the various GAGs were higher. The anti-cancer efficacy for fractions 5-7 were comparable Low Molecular Weight Heparin (LMWH) isolated from camel intestine (FIG. 5A).

Figure 8A:
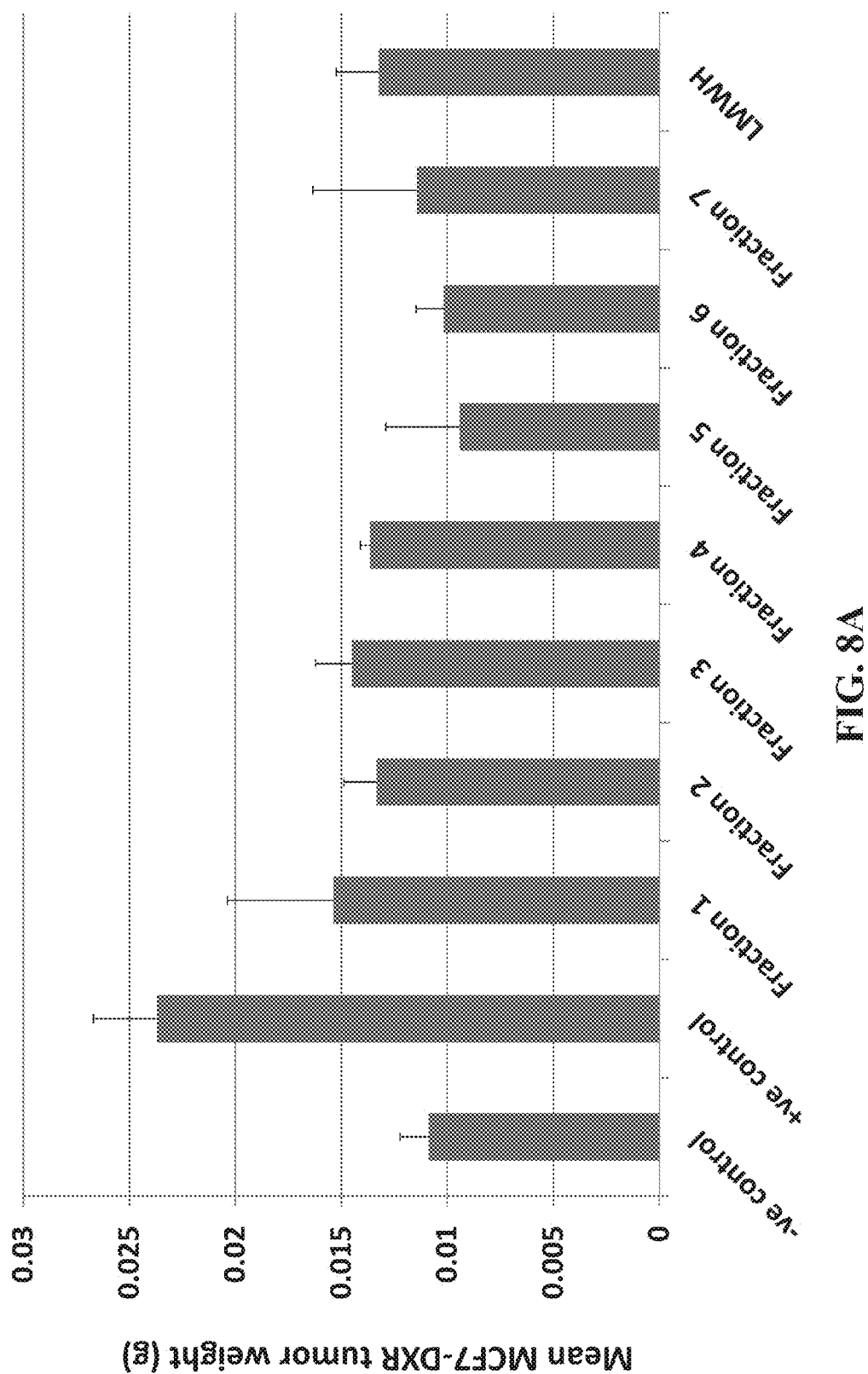
FIG. 8A depicts a bar graph demonstrating the anti-tumor effects of HPLC-SEC separated camel urine fractions on human chemo-resistant breast cancer cells (MCF7-Doxorubicin resistant) tumor growth in the CAM model, in accordance with embodiments of the present invention.

FIG. 8A depicts a bar graph demonstrating the anti-tumor effects of HPLC-SEC separated camel urine fractions (1-7) on human chemo-resistant breast cancer cells (MCF7-Doxorubicin resistant) tumor growth in the CAM model, in accordance with embodiments of the present invention.

Figure 5B:
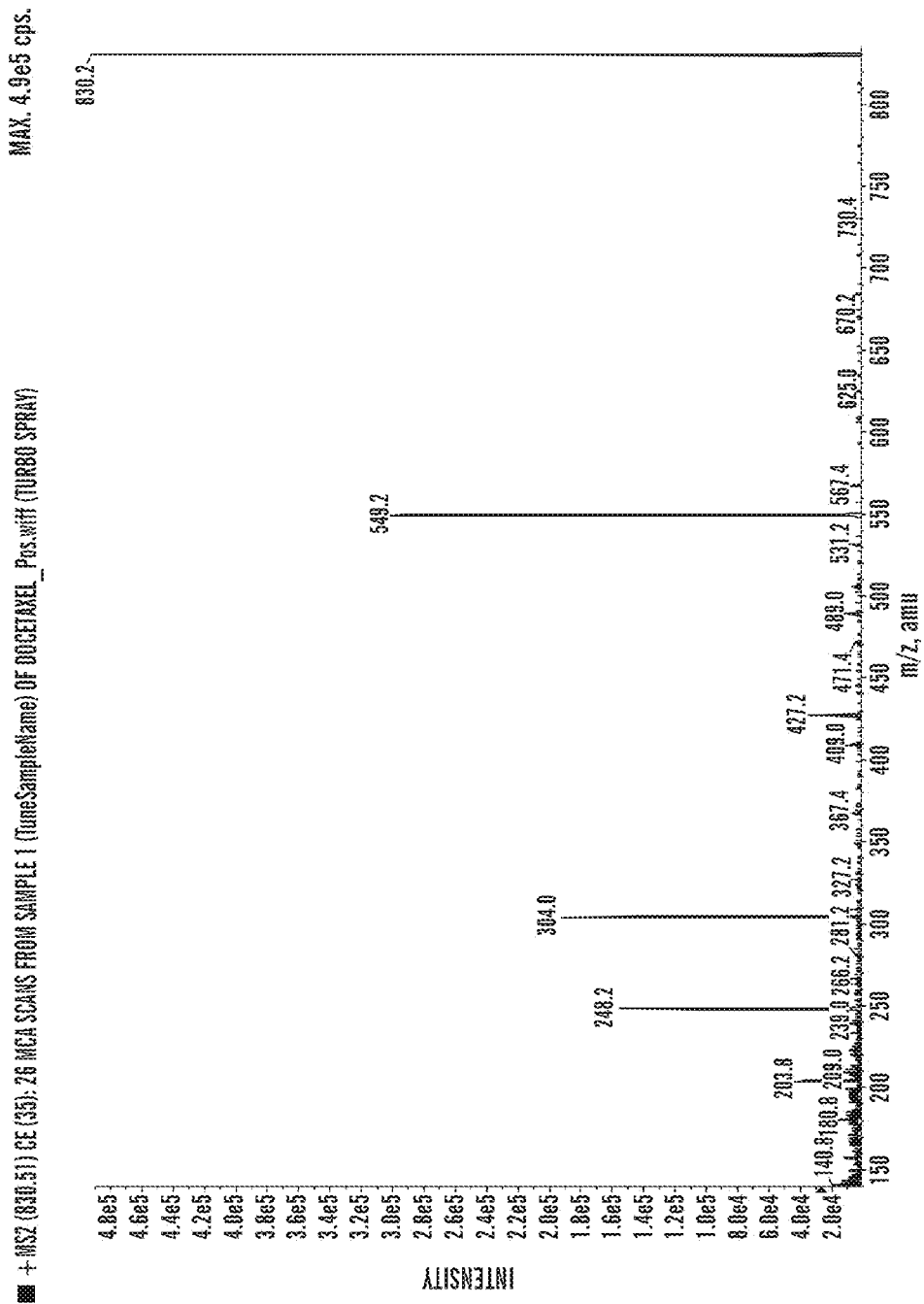
Figure 5C:
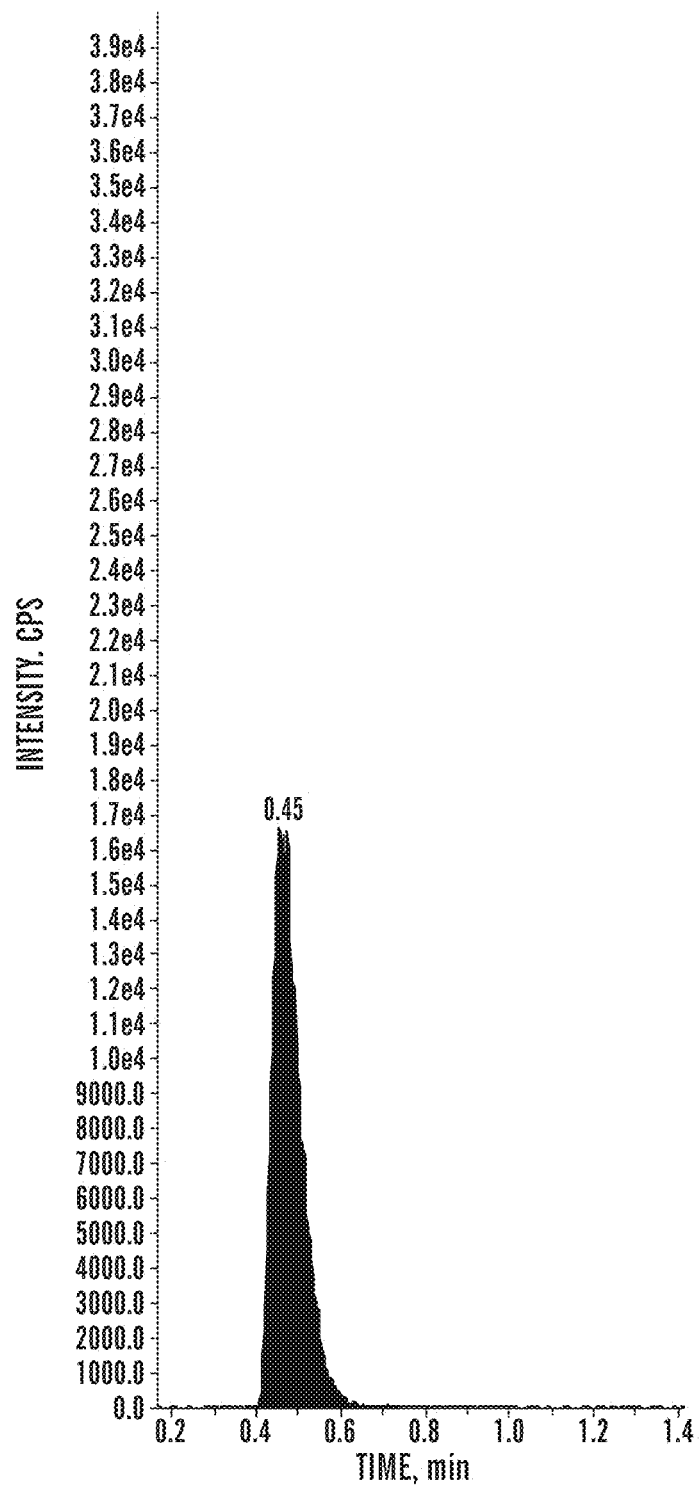
Figure 5C:
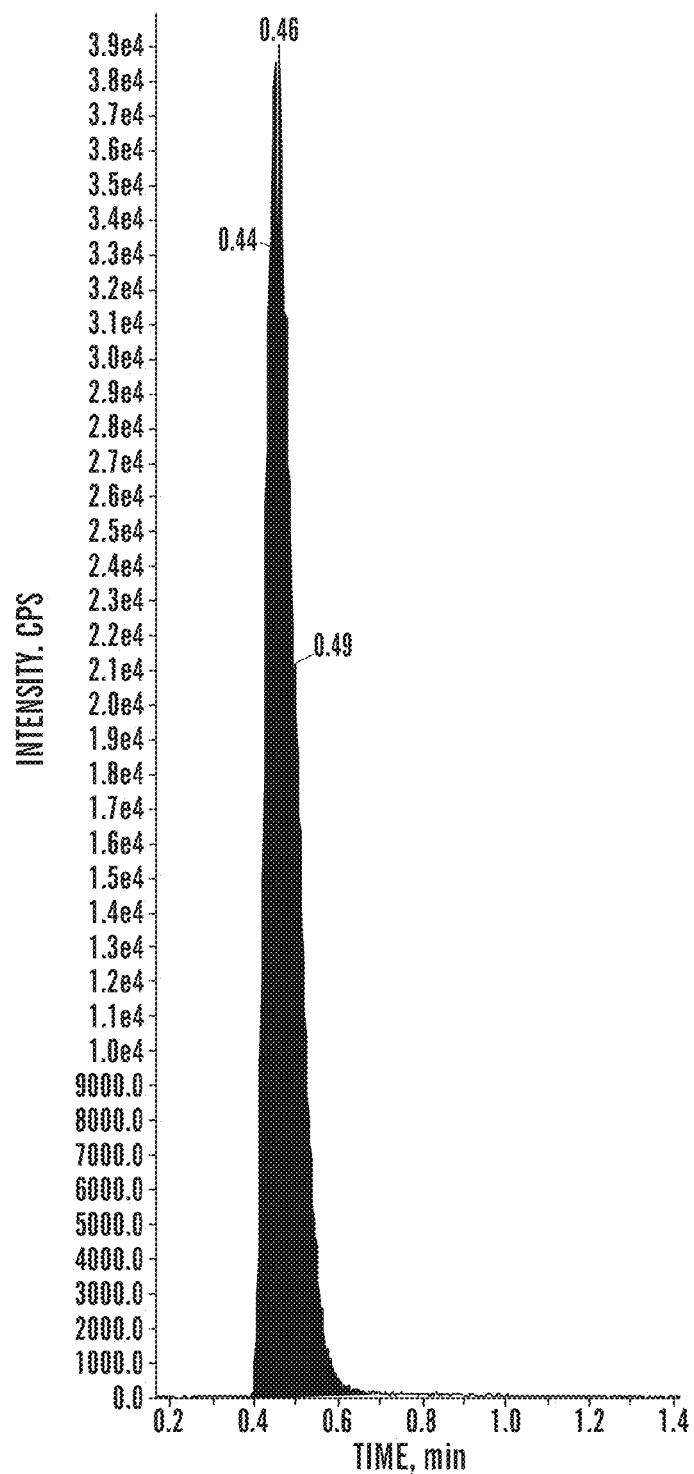
Figure 5C:
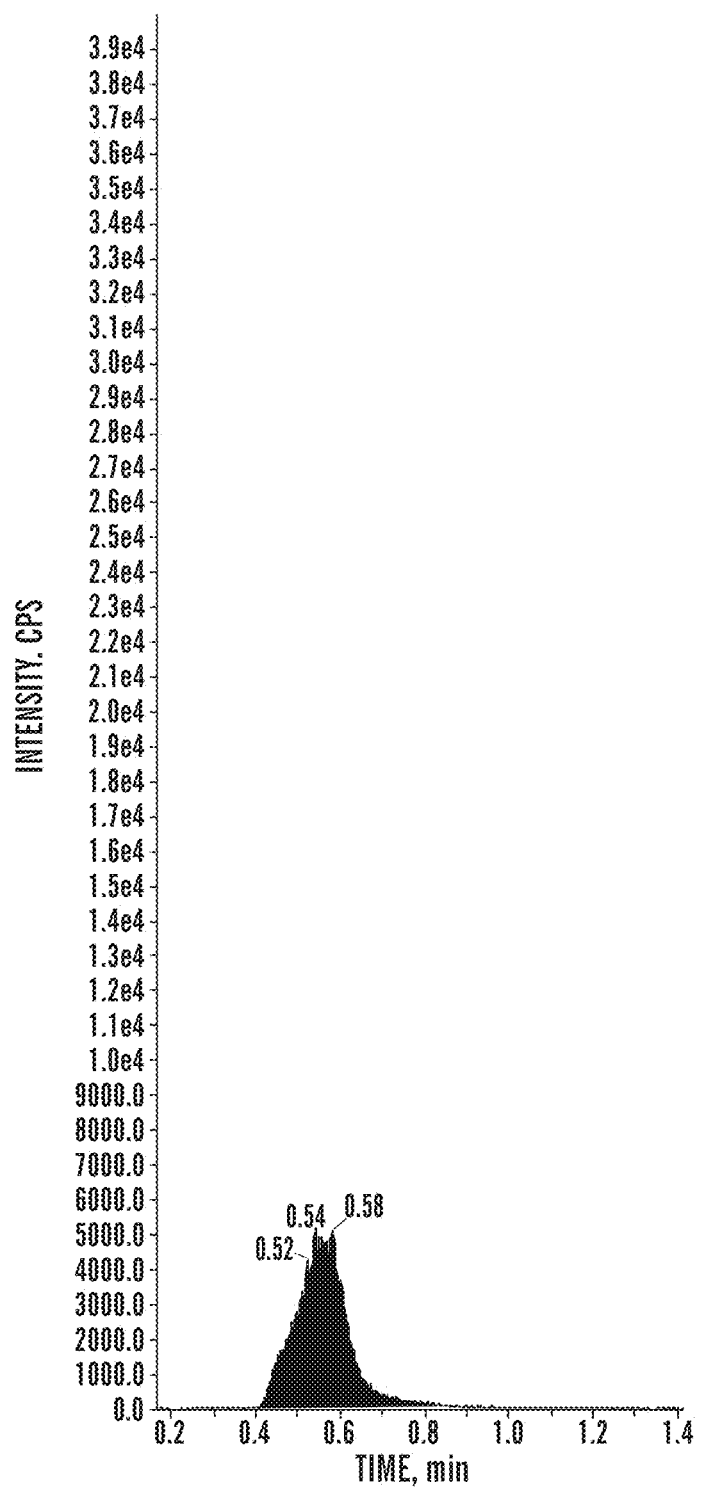
Figure 5C:
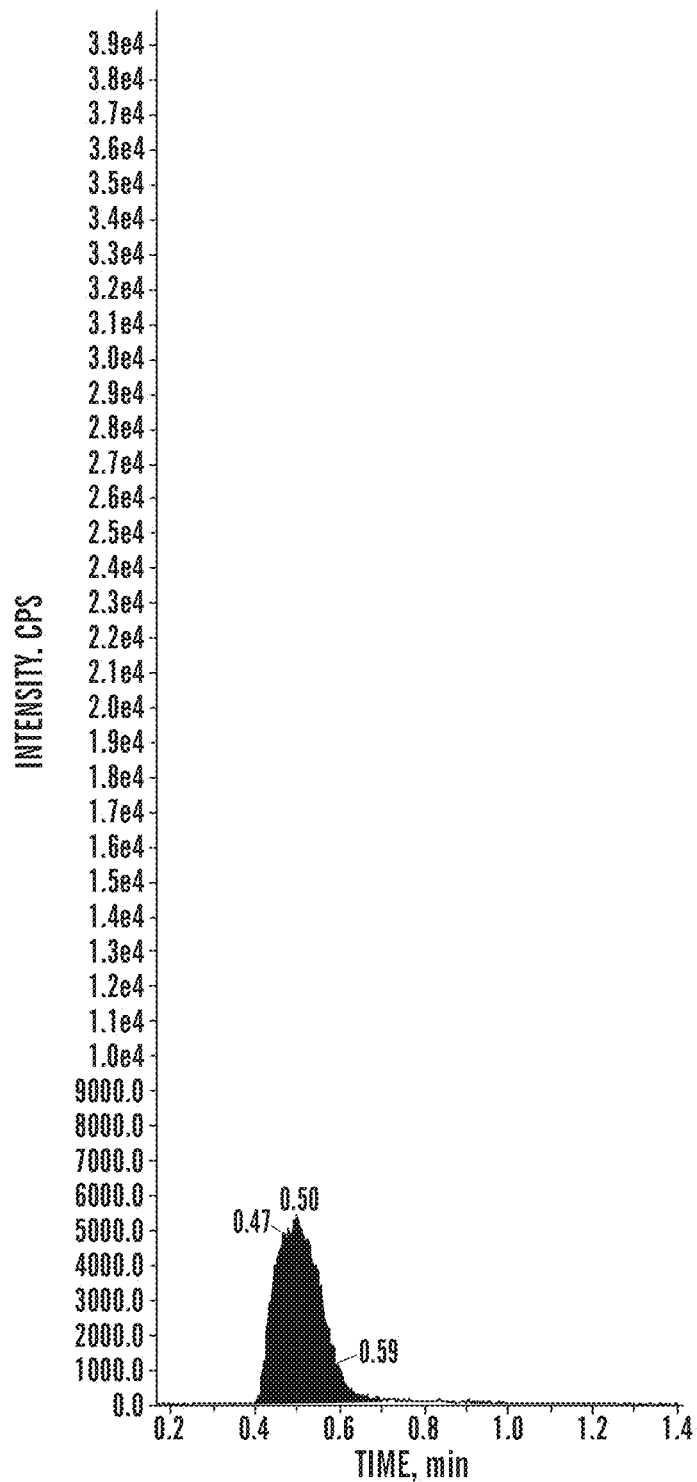

Furthermore, the data demonstrated significant inhibition of tumor angiogenesis for the different camel urine fractions against breast cancer (MCF7) breast cancer chemo-resistant cell line. Fractions 5-7 demonstrated greater anti-angiogenesis efficacy where the levels of the various GAGs were higher. The anti-angiogenesis efficacy for fractions 5-7 (100% inhibition back to control PBS level) were comparable Low Molecular Weight Heparin (LMWH) isolated from camel intestine (FIG. 5B).

Figure 8B:
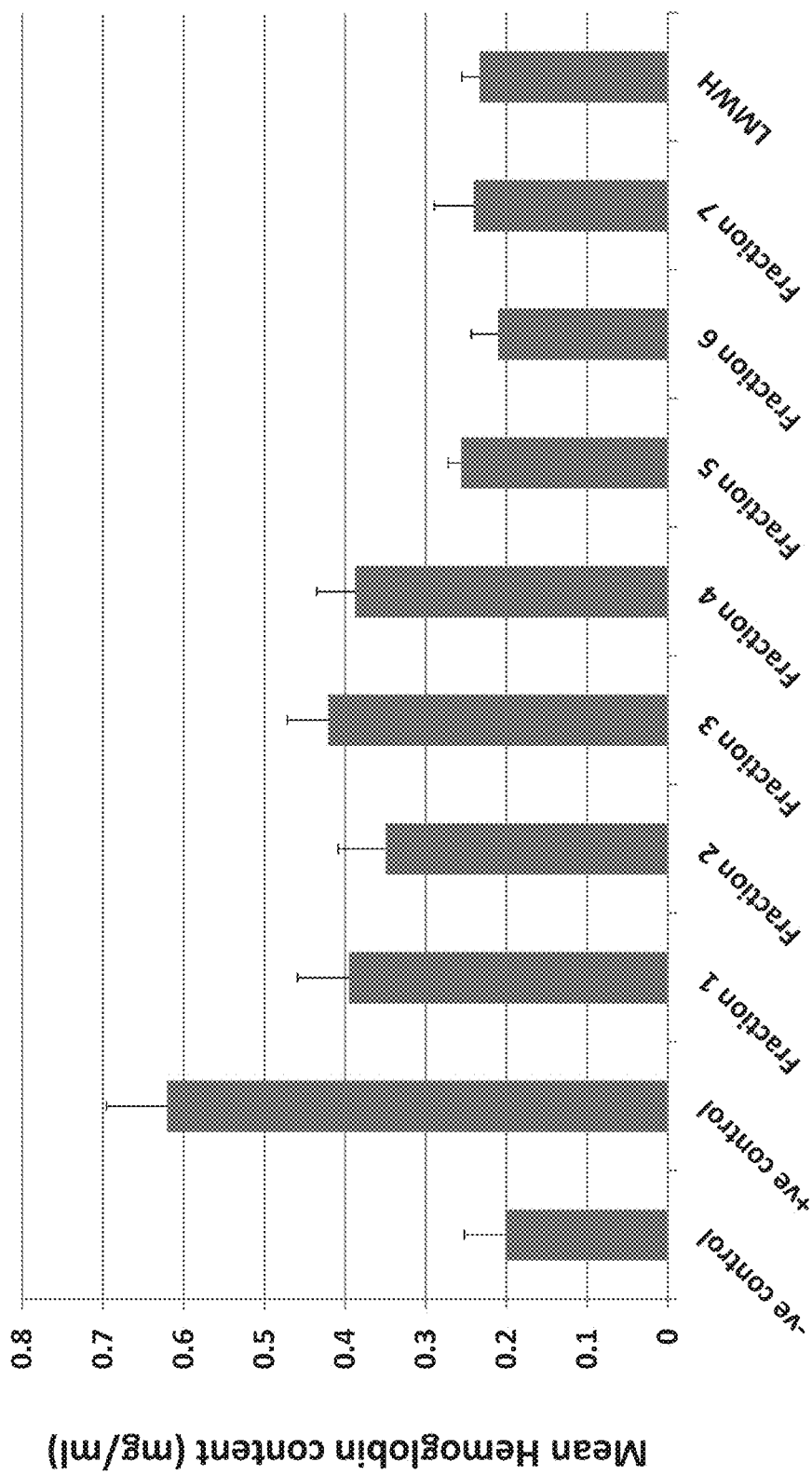
FIG. 8B depicts a bar graph demonstrating the effect of HPLC-SEC separated camel urine fractions on human chemo-resistant breast cancer cells (MCF7-Doxorubicin resistant) tumor angiogenesis in the CAM model, in accordance with embodiments of the present invention.

FIG. 8B depicts a bar graph the effect of HPLC-SEC separated camel urine fractions (1-7) on human chemo-resistant breast cancer cells (MCF7-Doxorubicin resistant) tumor angiogenesis in the CAM model, in accordance with embodiments of the present invention.

FIG. 8C illustrates the effect of HPLC-SEC separated camel urine fractions (1-7) versus LMWH on human chemo-resistant breast cancer cells (MCF7-Doxorubicin resistant) tumor angiogenesis in the CAM model, in accordance with embodiments of the present invention.

Example 34: Activated Partial Thromboplastin Time (aPTT)

To 0.1 ml of citrated plasma 0.1 ml of human placenta lipid is added and the mixture is incubated for 2 min at 37° C. The coagulation process is initiated by the addition of 0.1 ml 25 mM calcium chloride and the time to clot formation is determined. The APTT measures effects on the endogenous pathway of coagulation. Camel derived bio products in camel urine or camel milk significantly prolonged aPTT (FIG. 9).

Figure 9:
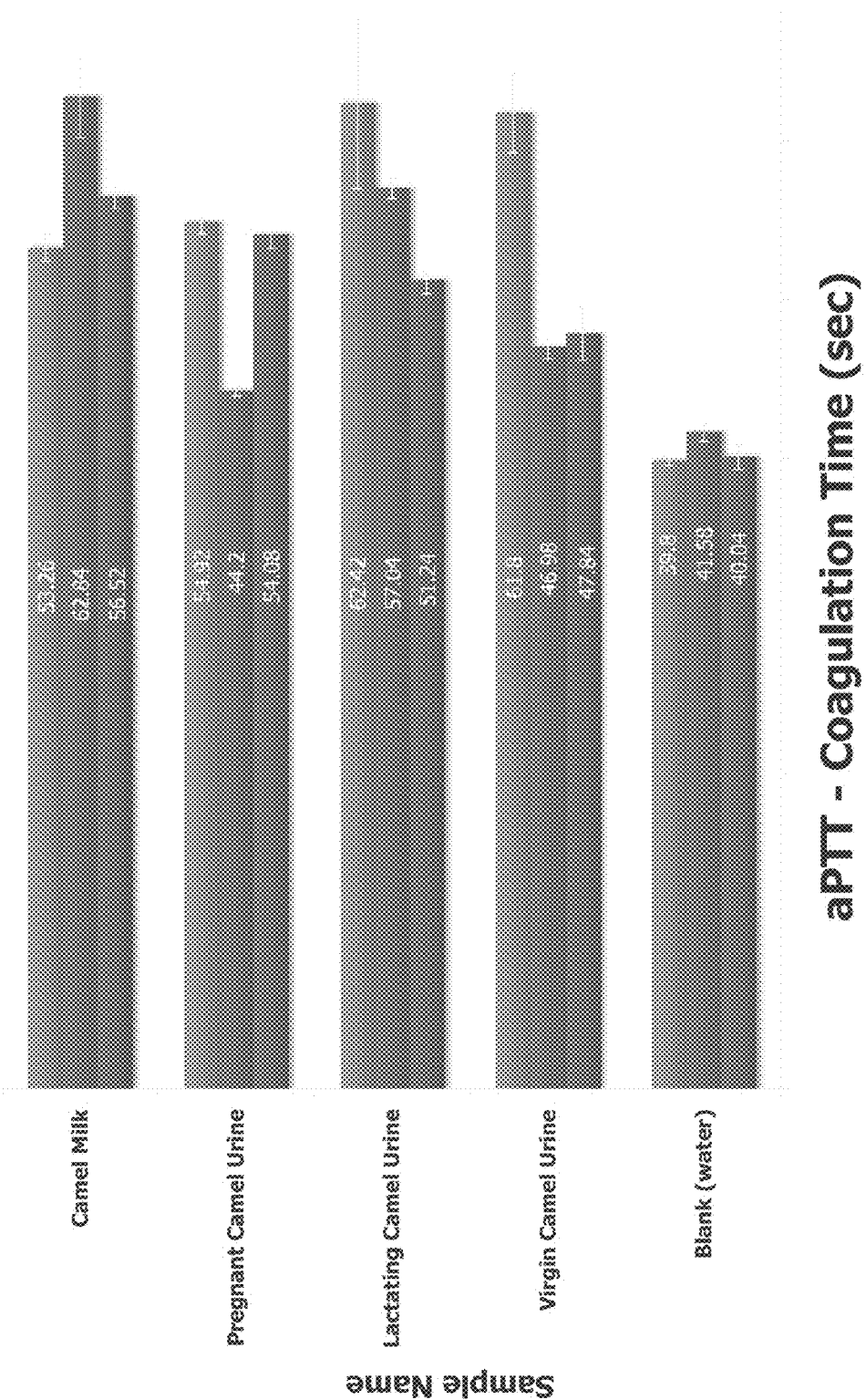
FIG. 9 provides an assessment of Anticoagulant Activity (aPTT) of bio products in Camel urine and milk demonstrating significant prolongation of aPTT above blank (control), in accordance with embodiments of the present invention.

FIG. 9 provides an assessment of Anticoagulant Activity (aPTT) of bio products in Camel urine and milk demonstrating significant prolongation of aPTT above blank (control), in accordance with embodiments of the present invention.

Example 34: Platelet-Fibrin Clot Kinetics

Thrombelastography (TEG) was performed in either citrated whole blood after re-calcification. The blood samples were mixed with 3.8% tri-sodium citrate solution (one part citrate solution to 9 parts blood) as anticoagulant. The citrated whole blood was re-calcified by adding 0.4 ml isotonic calcium chloride solution. An aliquot of 0.36 ml of the re-calcified whole blood was transferred to the pre-warmed cup of the thrombelastograph. The following measurements were the standard variables of TEG: (i) Reaction time (R): the time from sample placement in the cup until onset of clotting (defined as amplitude of 1 mm). This represents the rate of initial fibrin formation; (ii) Maximum amplitude (MA): greatest amplitude on the TEG trace, wherein MA represents the absolute strength of the fibrin clot and is a direct function of the maximum dynamic strength of fibrin and platelets.

Figure 10:
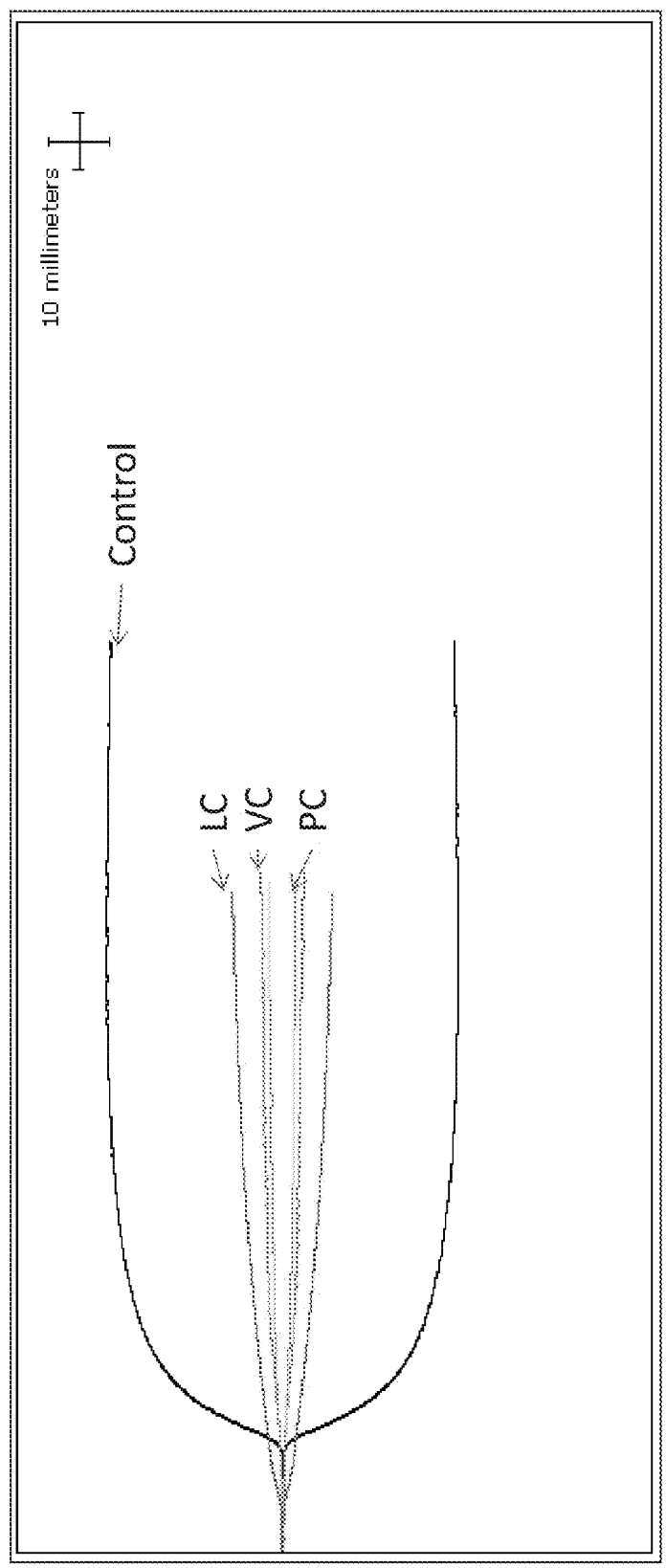
FIG. 10 illustrates the anti-coagulant activity of GAGs camel bio products in various camel urine including lactating camel (LC), Virgin camel (VC), and pregnant camel (PC)), in accordance with embodiments of the present invention.

The data demonstrated a significant inhibition of platelet-fibrin clot initiation (R) and strength (MA) as well as the rate of clot formation by urine bio products derived from various camels including lactating, virgin or pregnant (FIG. 10).

FIG. 10 illustrates the anti-coagulant activity of GAGs camel bio products in various camel urine including lactating camel (LC), Virgin camel (VC), and pregnant camel (PC)), in accordance with embodiments of the present invention.

Figure 11:
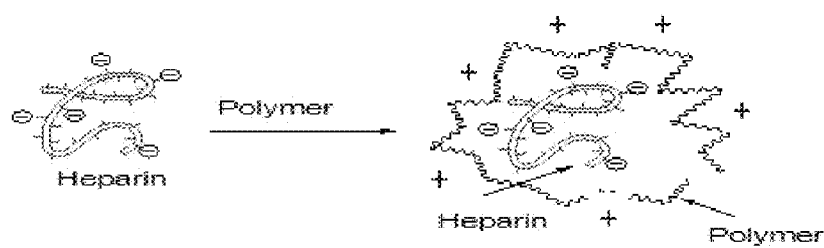
FIG. 11 is a diagram illustrating the camel derived glycosaminoglycans (GAG) ionic complex of heparin encapsulated into polymeric nanoparticles, in accordance with embodiments of the present invention.

FIG. 11 is a diagram illustrating the camel derived glycosaminoglycans (GAG) ionic complex of heparin encapsulated into polymeric nanoparticles, in accordance with embodiments of the present invention. The polymeric nanoparticles are denoted as "polymer" in FIG. 11. The GAG may be heparin (as shown), heparan sulfate, chondroitin/dermatan sulfate, Keratan sulfate, or hyaluronic acid. The polymeric nanoparticles may comprise lactoferrin or casein. The GAG is complexed ionically with the nanoparticle by electrostatic attraction between the negatively charged GAG and the positively charged nanoparticle (heparin in FIG. 11).

For FIG. 11, camel Lactoferrin (LF) and/or Casein (CA) or Low-molecular-weight chitosan (CS) nanoparticles is complexed via an ionic electrostatic interactions (ionically cross-linked) with camel derived GAGs and prepared by a physical self-assembly method. In practice, an aqueous solution of LF and/or CA or CS (pH 5.0, 2 mL) was combined with aqueous GAG such as heparin (5 mL) at various mass ratios and then magnetically stirred for 15 minutes at 30° C. The aggregates were removed by passing the solution through a 0.2 μm filter. Free heparin and LF and/or CA or CS were removed by washing the nanoparticles 3 times with distilled water and then the nanoparticles were collected by centrifugation at 30,000×g for 15 minutes.

Particle size, distribution, and zeta potential of heparin/LF and/or CA or CS nanoparticles were measured by laser diffraction Mastersizer (Malvern Instruments, PA). The morphology of nanoparticles was examined by atomic forced microscope or scanning electron microscope. The loading efficiency and loading content of heparin in tested nanoparticles were determined by the amount of free heparin left in the supernatant using the carbazole assay.

The nanoparticles may have a surface electric charge measured by zeta potential, which varies depending on the proportion of the LF and/or CA or CS and the GAG such as camel heparin in the nanoparticles. In one embodiment, the contribution to the positive charge of the nanoparticle is attributed to the amine groups of the chitosan, while the contribution to the negative charge of the GAG is attributed to the carboxylic and sulphate groups of the heparin. Depending on the LF and/or CA or CS/GAG proportion, the charge magnitude may vary between 0 mV and +40 mV, preferably between +1 and +25 mV. The positive surface charge of the nanoparticles improves the interaction between the nanoparticles and biological surfaces, particularly mucous surfaces, which are negatively charged, so that the biologically active molecule will favorably act on the target tissues.

Figure 12:
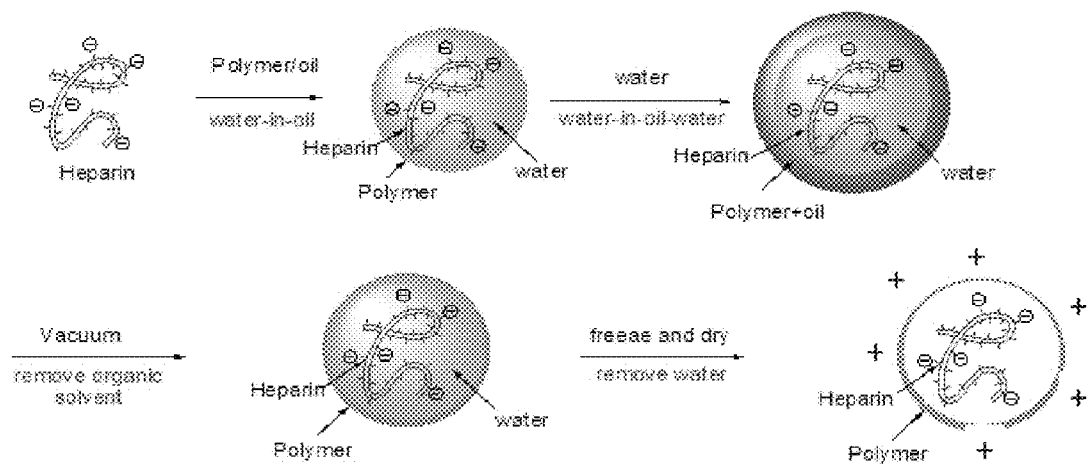
FIG. 12 depicts an encapsulation process for the formation of the camel derived GAG ionic complex encapsulated into cationic polymeric nanoparticles, in accordance with embodiments of the present invention.

FIG. 12 depicts an encapsulation process for the formation of the camel derived GAG ionic complex encapsulated into cationic polymeric nanoparticles, in accordance with embodiments of the present invention. The polymeric nanoparticles are denoted as "polymer". The GAG is complexed ionically with the nanoparticle by electrostatic attraction between the negatively charged GAG (heparin) and the positively charged nanoparticle.

For FIG. 12, in a single emulsification solvent evaporation process, polymer is dissolved in a volatile water immiscible organic solvent such as ethyl acetate, which is also used as the solvent for dissolving the hydrophobic surfactant. This solution was emulsified in an aqueous phase containing a surfactant or stabilizer (emulsifying agent) resulting in oil-in water (o/w) emulsion. The coalescence of the organic droplets was avoided by continuous stirring and emulsification and was enhanced by using sonication. After the formation of stable emulsion, the organic solvent is evaporated either under stirring at room temperature or by rotary evaporation under reduced pressure to transform the nano-emulsion into a nanoparticle suspension. Formed nanoparticles are separated from the aqueous slurry by centrifugation or lyophilization.

The present invention provides a composition. The composition comprises (i) polymeric nanoparticles and (ii) camel derived glycosaminoglycans (GAG)s ionic complex encapsulated into the nanoparticles, at least one active ingredient encapsulated into the nanoparticles, or combinations thereof.

In one embodiment, the polymeric nanoparticles are selected from the group consisting of lactoferrin nanoparticles comprising camel derived lactoferrin, casein nanoparticles comprising camel derived casein, and combinations thereof.

In one embodiment, the nanoparticles comprise the lactoferrin nanoparticles.

In one embodiment, the nanoparticles comprise the casein nanoparticles.

In one embodiment, the camel derived lactoferrin is lactoferrin derived from camel milk.

In one embodiment, the nanoparticles comprise the casein nanoparticles.

In one embodiment, the camel derived casein is casein derived from camel milk.

In one embodiment, the camel derived GAGs are encapsulated into the nanoparticles.

In one embodiment, the camel derived GAGs are selected from the group consisting of camel derived heparin/heparan sulfate (HSGAGs), chondroitin/dermatan sulfate (CSGAGs), Keratan sulfate, hyaluronic acid, and combination thereof.

In one embodiment, the camel derived GAGs comprise GAGs derived from camel milk.

In one embodiment, the nanoparticles are 50% to 90% by weight of the composition, and the GAGs are 10% to 50% by weight of the composition.

In one embodiment, the at least one active ingredient is encapsulated into the nanoparticles.

In one embodiment, the nanoparticles have an average particle size between 50 and 250 nm.

In one embodiment, the at least one active ingredient is selected from the group consisting of a moisturizer, a skin-lightening agent, a hair growth stimulant, a hair restorer, a hair growing agent, an anti-aging agent, an antioxidant, an anti-wrinkle agent, a skin softener, an anti-acne agent, an ultraviolet absorber, a cleansing agent regulator, and combination thereof.

In one embodiment, the at least one active ingredient is a functional food ingredient selected from the group consisting of a vitamin, a mineral, an antioxidant, an anti-stress agent, amino acids, carotenoid, fruit and vegetable extracts, and combination thereof.

In one embodiment, the at least one active pharmaceutical ingredient comprises green tea extract or pomegranate extract.

In one embodiment, the at least one active ingredient comprises a transdermal agent, a topical agent, an injectable, an oral therapeutic agent, or a supplement, or combinations thereof.

In one embodiment, the at least one active ingredient is an active pharmaceutical ingredient selected from the group consisting of a hair growth stimulant, an antibiotic, an anti-cancer agent, anti-viral, vaccine, an anti-inflammatory agent, an anti-allergic agent, a therapeutic agent for skin disease, an antifungal agent, an antipyretic, an analgesic, a muscle relaxant, a cold remedy, an anti-diabetic agent, a therapeutic agent for hyperlipidemia, an antitussive agent, antiplatelets, an anticoagulant, a hemostatic regulator, and combination thereof.

In one embodiment, the composition further comprises a cationic or anionic polysaccharide.

In one embodiment, the nanoparticles are electrically charged with a zerta potential between 0 mV and +40 mV, or between +1 mV and +25 mV.

The present invention provides a dairy product. The dairy product comprises ice cream or frozen yogurt, wherein the ice cream or frozen yogurt comprises any of the compositions of the present invention and is derived from camel milk or other species of milk (e.g., cow milk, goat milk, etc.).

The present invention provides a method for treating a disorder in a subject. The method comprises administering a therapeutic dose of the any of the compositions of the present invention.

In one embodiment, the subject is a mammal (e.g., a human being or a non-human mammal).

In one embodiment, the therapeutic dose is 1.0 to 100 mg per kilogram of body weight of the subject.

In one embodiment, the disorder is selected from the group consisting of cancer, a viral infection, a bacterial infection, a fungus infection, thrombosis, diabetes, hyperlipidemia, a vascular disorder, an inflammatory disorder, and combinations thereof.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising:
nanoparticles, wherein the nanoparticles are selected from the group consisting of lactoferrin nanoparticles comprising camel derived lactoferrin, casein nanoparticles comprising camel derived casein, and combinations thereof, wherein the nanoparticles have an average particle size between 50 and 250 nm; and
camel derived glycosaminoglycans (GAG)s encapsulated within the nanoparticles, wherein the nanoparticles are positively charged, the GAG is negatively charged, and the GAG is complexed ionically with the nanoparticle by electrostatic attraction between the negatively charged GAG and the positively charged nanoparticle.

2. The composition of claim 1, wherein the nanoparticles comprise the lactoferrin nanoparticles.

3. The composition of claim 2, wherein the camel derived lactoferrin is lactoferrin derived from camel milk.

4. The composition of claim 1, wherein the nanoparticles comprise the casein nanoparticles.

5. The composition of claim 1, wherein the camel derived GAGs are selected from the group consisting of camel derived heparin or heparan sulfate (HSGAGs), chondroitin or dermatan sulfate (CSGAGs), Kerman sulfate, hyaluronic acid, and combination thereof.

6. The composition of claim 1, wherein the camel derived GAGS comprise GAGs derived from camel milk.

7. The composition of claim 1, wherein the nanoparticles are 50% to 90% by weight of the composition, and the GAGs are 10% to less than 50% by weight of the composition.

8. The composition of claim 1, wherein the nanoparticles have an average particle size between 50 and 100 nm.

9. The composition of claim 1, wherein at least one active ingredient, in addition to the GAGs, is encapsulated within the nanoparticles.

10. The composition of claim 9, wherein the at least one active ingredient is selected from the group consisting of a moisturizer, a skin-lightening agent, a hair growth stimulant, a hair restorer, a hair growing agent, an anti-aging agent, an antioxidant, an anti-wrinkle agent, a skin softener, an anti-acne agent, an ultraviolet absorber, and combination thereof.

11. The composition of claim 9, wherein the at least one active ingredient is a functional food ingredient selected from the group consisting of a vitamin, a mineral, an antioxidant, an anti-stress agent, amino acids, carotenoid, fruit and vegetable extracts, and combination thereof.

12. The composition of claim 9, wherein the at least one active pharmaceutical ingredient comprises green tea extract or pomegranate extract.

13. The composition of claim 9, wherein the at least one active ingredient comprises a transdermal agent, a topical agent, an injectable, an oral therapeutic agent, or a supplement, or combinations thereof.

14. The composition of claim 9, wherein the at least one active ingredient is a an active pharmaceutical ingredient selected from the group consisting of a hair growth stimulant, an antibiotic, an anti-cancer agent, anti-viral, vaccine, an anti-inflammatory agent, an anti-allergic agent, a therapeutic agent for skin disease, an antifungal agent, an antipyretic, an analgesic, a muscle relaxant, a cold remedy, an anti-diabetic agent, a therapeutic agent for hyperlipidemia, an antitussive agent, antiplatelets, an anticoagulant, a hemostatic regulator, and combination thereof.

15. The composition of claim 1, further comprising a cationic or anionic polysaccharide.

16. The composition of claim 1, wherein the nanoparticles are electrically charged with a positive zeta potential between +1 mV and +25 mV.

17. A dairy product, comprising ice cream or frozen yogurt, said ice cream or frozen yogurt comprising the composition of claim 1 and being derived from camel milk.

* * * * *